(12) United States Patent
Bourles et al.

(10) Patent No.: US 11,590,243 B2
(45) Date of Patent: Feb. 28, 2023

(54) FORMULATION

(71) Applicant: GLAXOSMITHKLINE BIOLOGICALS S.A., Rixensart (BE)

(72) Inventors: Erwan Bourles, Rixensart (BE);
Olivier Despas, Rixensart (BE);
Delphine Guillaume, Rixensart (BE);
Frederic Mathot, Rixensart (BE);
Mathieu Vasselle, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 722 days.

(21) Appl. No.: 16/478,232

(22) PCT Filed: Jan. 25, 2018

(86) PCT No.: PCT/IB2018/050453
§ 371 (c)(1),
(2) Date: Jul. 16, 2019

(87) PCT Pub. No.: WO2018/138667
PCT Pub. Date: Aug. 2, 2018

(65) Prior Publication Data
US 2019/0365930 A1    Dec. 5, 2019

(30) Foreign Application Priority Data
Jan. 25, 2017 (GB) .................................. 1701239

(51) Int. Cl.
| | | |
|---|---|---|
| *A61K 39/395* | (2006.01) | |
| *A61K 48/00* | (2006.01) | |
| *A61K 9/00* | (2006.01) | |
| *A61K 9/08* | (2006.01) | |
| *A61K 9/19* | (2006.01) | |
| *A61K 47/02* | (2006.01) | |
| *A61K 47/26* | (2006.01) | |
| *C12N 15/86* | (2006.01) | |

(52) U.S. Cl.
CPC ........ *A61K 48/0091* (2013.01); *A61K 9/0019* (2013.01); *A61K 9/08* (2013.01); *A61K 9/19* (2013.01); *A61K 47/02* (2013.01); *A61K 47/26* (2013.01); *C12N 15/86* (2013.01); *C12N 2710/10132* (2013.01); *C12N 2710/10143* (2013.01)

(58) Field of Classification Search
None
See application file for complete search history.

(56) References Cited

U.S. PATENT DOCUMENTS

| | | | |
|---|---|---|---|
| 6,258,362 B1 * | 7/2001 | Loudon ................... | A61P 31/22 435/14 |
| 2005/0186225 A1 | 8/2005 | Evans et al. | |
| 2010/0260796 A1 | 10/2010 | Belin-Poput et al. | |
| 2016/0228369 A1 | 8/2016 | Qiao et al. | |

FOREIGN PATENT DOCUMENTS

| | | |
|---|---|---|
| CN | 101312742 A | 11/2008 |
| CN | 102028954 A | 4/2011 |
| CN | 102631672 A | 8/2012 |
| CN | 105112428 A | 12/2015 |
| CN | 105636610 A | 6/2016 |
| JP | 2005-523233 A | 8/2005 |
| JP | 2007-518414 A | 7/2007 |
| JP | 2012-516679 A | 7/2012 |
| WO | WO 03/000283 A1 | 1/2003 |
| WO | WO 2005/071093 A2 | 8/2005 |
| WO | WO 2010/086189 A2 | 8/2010 |
| WO | WO 2015/189425 A | 12/2015 |

OTHER PUBLICATIONS

Pastorino, et al., PLOS One, 2015, vol. 10, No. 4, pp. 1-12.
Searles, et al., J of Pharma Sci, 2001, vol. 90, No. 7, pp. 872-887.
Croyle, Maria A., "Factors that Influence Stability of Recombinant Adenoviral Preparations for Human Gene Therapy" Pharmaceutical Development and Technology, 3(3), 1998. pp. 373-383.
Tao et al., "Preparation of freeze-dried recombinant adenovirus expressing hypoxia inducible factor-1 alpha of triple mutant," The Journal of Practical Medicine, vol. 27, No. 3, 2011, pp. 369-371, 3 pages total, with an English abstact.
Communication Pursuant to Article 94(3) EPC dated Jun. 2, 2022, in European Patent Application No. 18 703 633.0-1109.

\* cited by examiner

*Primary Examiner* — Yunsoo Kim
(74) *Attorney, Agent, or Firm* — Birch, Stewart, Kolasch & Birch, LLP

(57) ABSTRACT

The present invention relates to the formulation of adenoviral vectors in sorbitol containing compositions in combination with a further amorphous sugar, its formulation as well as a method for obtaining a dried composition.

18 Claims, 21 Drawing Sheets

UPLC-bio content (% recovery) vs. Time point

ASPECT

| Overage | | Formulation: T=18 | | Formulation: T=23 | |
|---|---|---|---|---|---|
| | | 15 | 25 | 15 | 25 |
| 100 S- | | OOO | OOO | O+XX / XXX | XXX |
| 50 S- | | OOO | OOO | OXX | X+X / XXX |
| 50 S+ | | OOX | O+X / XXX / OXX | XXX | XXX |

Secondary Dessication Temperature

O = Intact
+ = Cracked
X = Fragmented

*Figure 20*

POWDERY

| Overage | Formulation: T=18 | | Formulation: T=23 | |
|---|---|---|---|---|
| | 15 | 25 | 15 | 25 |
| 100 S- | O O O | + X O | + X X | O X X |
| 50 S- | X + X | O O X | + X X | X X X |
| 50 S+ | O + X | O X X | + X X | O X X |

Secondary Dessication Temperature

O = Not Powdery
+ = Slightly Powdery
X = Powdery

*Figure 21*

FORMULATION

This application is a National Stage entry under U.S.C. § 371 of PCT/IB2018/050453, filed Dec. 8, 2017, which claims priority to GB 1701239.4, filed Jan. 25, 2017.

The present invention relates to the formulation of adenoviral vectors in freeze dried compositions, their formulations as well as methods for obtaining the freeze-dried composition.

BACKGROUND

Adenoviral vectors represent a prophylactic or therapeutic protein delivery platform whereby the nucleic acid sequence encoding the prophylactic or therapeutic protein is incorporated into the adenoviral genome, which is brought to expression when the adenoviral particle is administered to the treated subject. It has been a challenge in the art to develop stabilizing formulations for the adenoviral vectors which allow storage at acceptable storage temperatures with a considerable shelf life.

Stabilizing formulations have been reported for human adenoviral vectors such as described by R. K Evans et al. ('Development of stable Liquid Formulations for Adenovirus-Based Vaccines' *Journal of Pharmaceutical Sciences* (2004) Vol. 93, No. 10, 2458-2475). However, there remains a need in the art for formulations preserving the stability of adenoviral vectors.

SUMMARY OF THE INVENTION

The inventors surprisingly found that the use of sorbitol in the formulation of simian adenoviral vectors substantially improves stability throughout lyophilisation, especially in combination with the amorphous sugar trehalose as a further cryoprotectant. The invention therefore provides an aqueous mixture for lyophilisation and a freeze-dried composition obtained from said aqueous mixture by lyophilisation (hereinafter referred to as the "dried composition") comprising sorbitol in combination with a further amorphous sugar acting as a cryoprotectant, such as trehalose.

In addition it has been found that having low salt content has further favourable effects on the stability of the simian adenoviral vector particles, especially on stability during freeze-drying and upon reconstitution of the lyophilised cake. Thus the invention further provides the adenoviral compositions containing sorbitol and a further amorphous sugar also comprising a low amount of NaCl. The invention also provides a method of using the freeze-dried composition whereby the composition is reconstituted with a low salt aqueous liquid, e.g. water for injection or an aqueous solution of a non-ionic isotonifying agent.

The invention further provides a method of lyophilisation of the described adenoviral vector compositions.

BRIEF DESCRIPTION OF THE DRAWINGS

FIG. 20—aspect of lyophilised adenovirus formulated with 18% trehalose+3.5% sorbitol (left panels) or 23% trehalose (right panels) at secondary drying temperatures of 15° C. or 25° C. after simulation of two hours road transport and two hours air transport. Vials were either siliconized (S+) or not siliconized (S−). Siliconized vials were loaded with an overage of 50% and non-siliconized vials were loaded with an overage of either 50% or 100%. (O)=intact; (+)=cracked; (X)=fragmented.

FIG. 21—consistency of lyophilised adenovirus formulated with 18% trehalose+3.5% sorbitol (left panels) or 23% trehalose (right panels) at secondary drying temperatures of 15° C. or 25° C. after simulation of two hours road transport and two hours air transport. Vials were either siliconized (S+) or not siliconized (S−). Siliconized vials were loaded with an overage of 50% and non-siliconized vials were loaded with an overage of either 50% or 100%. (O)=not powdery; (+)=slightly powdery; (X)=powdery.

DETAILED DESCRIPTION

Figure 1:
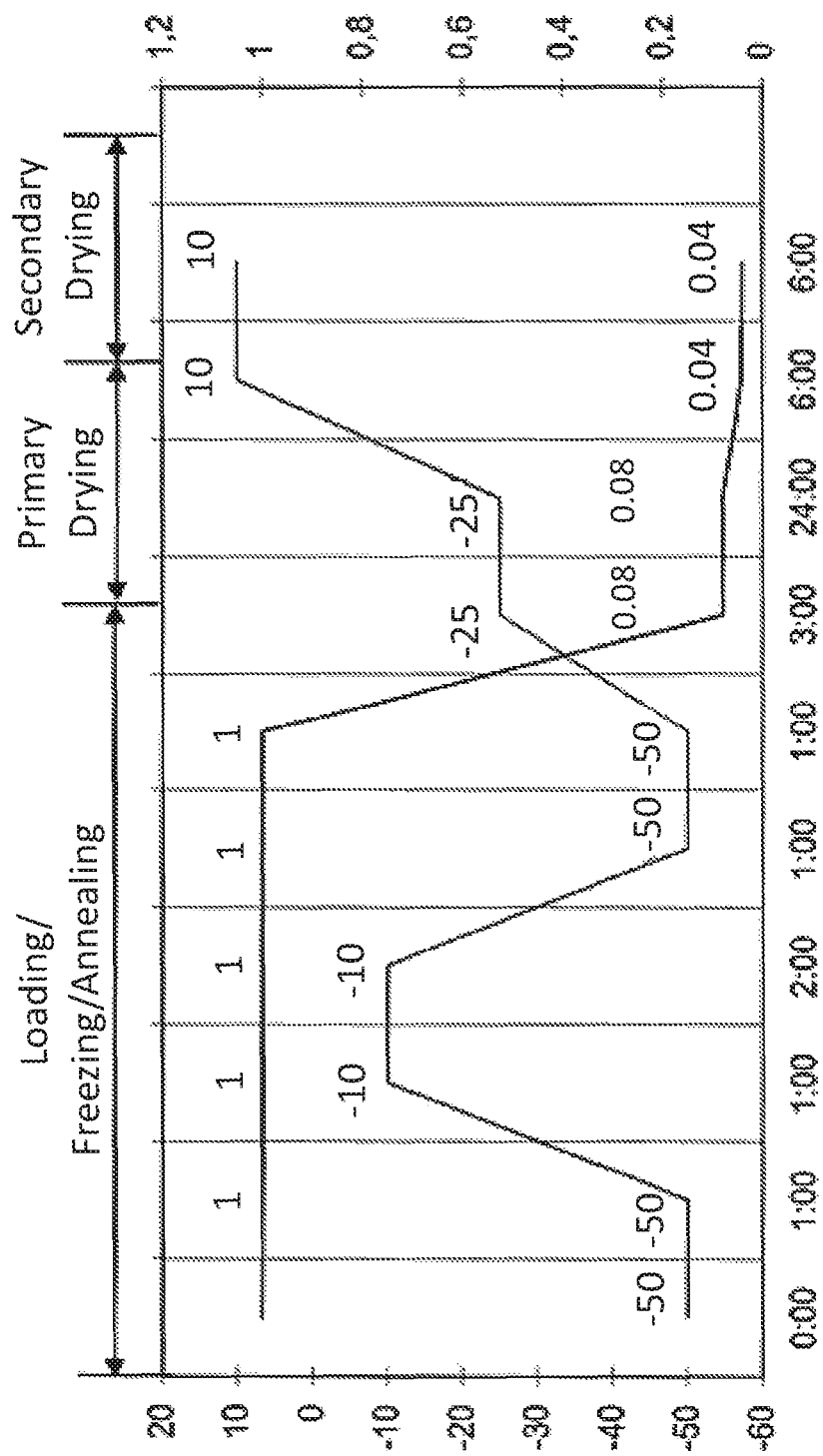
FIG. 1—illustration of the freeze drying cycle as used in Example 1.

Contrary to reports in the art on the formulation of adenoviral vectors, the inventors found that the stabilizing formulations developed for e.g. human adenoviral vectors could not successfully be applied to all adenoviral vectors, e.g. simian adenoviral vectors. The present invention now describes compositions of adenoviral vectors wherein the adenoviral particle's structural integrity and functionality is better protected or maintained.

The inventors found that adding sorbitol in combination with a further amorphous sugar when formulating adenoviral vectors, and in particular simian adenoviral vectors, for freeze-drying, increases stability of that adenoviral vector upon freeze-drying and/or during further storage.

Both sorbitol and the further amorphous sugar are considered to be cryoprotectants. The term "cryoprotectant" refers to a class of excipients which prevents freeze damage of what is being frozen, in casu, the adenoviral vector.

An amorphous sugar suitable for use according to the present invention in combination with sorbitol may be selected from sucrose, trehalose, mannose, mannitol, raffinose, lactitol, lactobionic acid, glucose, maltulose, isomaltulose, lactulose, maltose, lactose, isomaltose, maltitol, palatinit, stachyose, melezitose, dextran, or a combination thereof. In one embodiment, the amorphous sugar is selected from sucrose, trehalose, lactose, raffinose, dextran and combinations thereof.

In a specific embodiment, the further amorphous sugar in combination with sorbitol is trehalose or sucrose, or, trehalose in combination with a second amorphous sugar such as selected from sucrose, lactose, raffinose, dextran and mannitol. Alternatively, the amorphous sugar is trehalose, sucrose or combination of sucrose and trehalose. In another embodiment, the amorphous sugar is trehalose or trehalose in combination with sucrose. In yet another embodiment, the amorphous sugar is trehalose.

Sorbitol and the selected amorphous sugar, e.g. trehalose, may be present in a defined ratio. In an embodiment, the ratio of sorbitol to amorphous sugar is 4/10 or below, 4/12 or below, 4/13 or below, 4/14 or below. In another embodiment, the ratio of sorbitol to amorphous sugar is between 4/10 and 3/23, between 4/12 and 4/23, between, 4/13 and 4/20, between 4/14 and 4/18, between 4/14 and 3.5/16, or between 4/14 and 4/16. In a specific embodiment the ratio is between 4/14 and 4/16. In a further specific embodiment, the amorphous sugar is trehalose and the ratio sorbitol to trehalose is between 4/14 and 4/16.

Sorbitol may be present in defined amounts in the aqueous mixture from which the composition is freeze-dried. In an embodiment, the aqueous mixture contains between 2 and 4% (w/v), between 2.5 and 4% (w/v) or between 3 and 4% (w/v) of sorbitol. In a specific embodiment, sorbitol is present in an amount between 3 and 4% (m/v).

The amorphous sugar as selected according to the embodiments herein may be present in defined amounts. In an embodiment, the aqueous mixture contains at least 3% (w/v), at least 5% (w/v), at least 10% (w/v), at least 11% (w/v), at least 12% (w/v), at least 13% (w/v), or at least 14% (w/v) of the amorphous sugar as selected herein above. In another embodiment the selected amorphous sugar is present in the aqueous mixture in a total amount of less than 23% (w/v), such as less than 20% (w/v), less than 18% (w/v), less than 17% (w/v), less than 16% (w/v), or less than 15% (w/v). Alternatively stated, the amorphous sugar is present in the aqueous mixture in a total amount of 23% or less (w/v), such as 20% or less (w/v), 18% or less (w/v), 17% or less (w/v), 16% or less (w/v), or 15% or less (w/v). Alternatively stated, the amorphous sugar can be present in the aqueous mixture in a total amount of at least 12%, at least 13% or at least 14% (w/v), but less than 18%, less than 17%, or less than 16% (w/v).

In a specific embodiment, the amorphous sugar is trehalose and is present in an amount between 12% and 18% (w/v), or, between 14% and 16.5% (w/v).

The inventors further found that adenoviral vectors can be substantially impacted by the presence of salt, such as sodium chloride, either when in dry or when in liquid form. The invention thus further relates to formulations, i.e. aqueous mixtures for lyophilisation and dried compositions as described herein, taking into account the sensitivity of adenoviral vectors to salt, such as sodium chloride. In one embodiment, simian adenoviral vectors are formulated using the aqueous mixtures and dried compositions described herein.

The term "salt" as used herein refers to ionic compounds that result from the neutralization reaction of an acid and a base, composed of a related number of cations and anions such that the product is without net charge, for example sodium chloride. The component ions can either be inorganic or organic, and, can be monoatomic or polyatomic.

According to one embodiment, the amount of salt, in particular the amount of NaCl, present in the aqueous mixture is defined to be less than 50 mM, less than 40 mM, less than 30 mM, less than 20 mM, less than 15 mM, less than 10 mM, or, less than 7.5 mM. Alternatively stated, the amount of NaCl, present in the aqueous mixture may be defined to be 50 mM or less, 40 mM or less, 30 mM or less, 20 mM or less, 15 mM or less, 10 mM or less, or, 7.5 mM or less. Preferably the composition is not completely devoid of salt or not completely devoid of NaCl. For the avoidance of doubt concerning to each of the embodiments relating the content of salt and NaCl in particular, it is understood that salt, respectively NaCl, is present in a measurable amount. Therefore according to an embodiment of the invention, salt, in particular sodium chloride, is present in an amount of at least 0.5 mM, at least 1 mM, at least 2 mM, at least 3 mM, or, at least 4 mM. Alternatively, sodium chloride is present in an amount between 1 and 50 mM, between 2.5 and 25 mM, between 2.5 and 15 mM, between 2.5 and 10 mM or between 2.5 and 7.5 mM. According to a particular embodiment, sodium chloride is present in an amount of about 5 mM, e.g. 5+/−0.5 mM.

For the purpose of defining ranges, the term "between" as used herein is considered to include the end points of the range. For example, when sodium chloride is said to be present in an amount between 2.5 and 10 mM, those formulations wherein NaCl is present at a concentration of 2.5 mM or 10 mM are included.

According to further embodiments, also the salt, such as sodium chloride, content of the aqueous liquid or diluent for reconstituting the dried composition is defined. By reconstituting a freeze-dried composition is meant rehydrating the dried composition to obtain a liquid mixture again. According to one embodiment the amount of salt, e.g. sodium chloride, present in the aqueous liquid for reconstituting is less than 50 mM, less than 40 mM, less than 30 mM, less than 20 mM, less than 15 mM, less than 10 mM, or, less than 7.5 mM, 50 mM or less, 40 mM or less, 30 mM or less, 20 mM or less, 15 mM or less, 10 mM or less or 7.5 mM or less.

The aqueous liquid for reconstituting the lyophilised composition may be essentially free of salt such as essentially free of sodium chloride. By essentially free is meant that the concentration of salt or sodium chloride is at or very near to zero mM. In a particular embodiment, the freeze-dried composition can be reconstituted with water for injection (WFI).

In a further embodiment, the aqueous liquid for reconstituting the composition is not completely devoid of salt or sodium chloride. Accordingly, salt, such as sodium chloride, can be present in the aqueous liquid used for reconstituting the dried composition in an amount of at least 0.5 mM, at least 1 mM, at least 2 mM, at least 3 mM, or, at least 4 mM. Alternatively, salt, such as sodium chloride, is present in the aqueous liquid used for reconstituting the composition in an amount between 1 and 50 mM, between 2.5 and 25 mM, between 2.5 and 15 mM, between 2.5 and 10 mM or between 2.5 and 7.5 mM. According to a particular embodiment, salt, such as sodium chloride, is present in the aqueous liquid used for reconstituting the composition in an amount of 5 mM.

The invention thus also provides a method of using the dried composition as described herein, wherein the dried composition is reconstituted with an aqueous liquid for reconstituting the composition as defined herein.

The aqueous mixture or dried composition may further include a surfactant selected from poloxamer surfactants (e.g. poloxamer 188), polysorbate surfactants (e.g. polysorbate 80 and/or polysorbate 20), octoxinal surfactants, polidocanol surfactants, polyoxyl stearate surfactants, polyoxyl castor oil surfactants, N-octyl-glucoside surfactants, macrogol 15 hydroxy stearate, and combinations thereof. In an embodiment, the surfactant is selected from poloxamer surfactants (e.g. poloxamer 188), polysorbate surfactants (e.g. polysorbate 80 and/or polysorbate 20), in particular polysorbate surfactants such as polysorbate 80.

In one embodiment, the surfactant is present in an amount of at least 0.001%, at least 0.005%, at least 0.01% (w/v), and/or up to 0.5% (w/v) as calculated with respect to the aqueous mixture. The surfactant can be present in an amount less than 0.25% or less than 0.1% (w/v). In another embodiment, the surfactant is present in an amount of 0.02% (w/v).

According to specific embodiments, the surfactant is polysorbate 80 or poloxamer 188 present in the aqueous mixture in an amount between 0.005% and 0.5% (w/v), such as about 0.02% (w/v).

In a further embodiment, a buffer is added to the aqueous mixture or dried composition. The pH is typically adjusted in view of the therapeutic components of the composition. Suitably, the pH of the aqueous mixture is at least 6, at least 6.5, at least 7 or at least 7.5. Alternatively stated, the pH of the aqueous mixture may be less than 10, less than 9.5, less than 9 or less than 8.5. In other embodiments, pH of the aqueous mixture is between 6 and 10, between 7 and 9.5, between 7.5 and 9.5, or, about 7.5, for example 7.5+/−0.5, or, 8.5+/−0.5. The optimal pH is in part also determined by the specific adenoviral vector formulated and/or the transgene incorporated therein.

An appropriate buffer may be selected from Tris, succinate, borate, Tris-maleate, lysine, histidine, glycine, glycylglycine, citrate, carbonate, phosphate or combinations thereof. In one embodiment, the buffer is Tris, succinate or borate. In a further embodiment, the buffer is Tris.

The buffer can be present in the aqueous mixture in an amount of at least 0.5 mM, at least 1 mM, at least 2 mM or at least 5 mM. Or, the buffer can be present in the aqueous mixture in an amount of less than 50 mM, less than 40 mM, less than 30 mM or less than 20 mM. For example, the buffer may be present in an amount of 0.5 mm to 50 mM, 1 mM to 50 mM or 2 mM to 20 mM. In one embodiment, the buffer is present in an amount of about 10 mM.

According to specific embodiments, the buffer is Tris, present in the aqueous mixture in an amount between 2 and 20 mM, such as at about 10 mM.

In an embodiment, the composition also comprises histidine in an amount of up to or about 20 mM, such as at a concentration of about 10 mM.

According to further embodiments, the composition also comprises bivalent metal ions, such as Mg2+, Ca2+, or Mg2+ or Ca2+ in the form of a salt, such as MgCl2, CaCl2) or MgSO4. In one embodiment the bivalent metal ion is Mg2+. Typical amounts wherein the bivalent metal ions are present in the aqueous mixture are between 0.5 and 10 mM, such as 1 or 2 mM, or 1 mM in particular.

For the purpose of describing embodiments of the invention and absent any indication to the contrary, the specified amounts of excipients considered for inclusion in the composition (i.e. salt, sodium chloride, cryoprotectant, buffer, surfactant and others described herein) are typically (and unless otherwise indicated) expressed as w/v % calculated with respect to the volume of the aqueous mixture. Alternatively, in case the aqueous mixture is freeze-dried and reconstituted, the amount of excipients may be expressed as w/v % calculated relative to the volume of the reconstituted composition.

In addition to the increased stability during the freeze-drying process, the novel formulation may also increase stability of the adenoviral vector upon storage of the freeze-dried composition. The novel formulation allows storage of the composition, liquid or dried, at 4° C., 25° C. or 37° C., for up to 1 month, 3 months, 6 months, 1 year, 2 years or 3 years. In one embodiment, the dried composition can be stored at 4° C. for 3 years, at 25° C. for 3 months or at 37° C. for 1 month. It is understood that storage is adequate if at least 50%, at least 60%, at least 70%, at least 80% or at least 90% of the infectivity is retained compared to the infectivity of the starting material.

The mixtures, compositions and methods described herein allow storage of the adenoviral vector for at least 1 month at 37° C., or at least 3 months at 25° C. or at least 3 years at 4° C. whilst retaining at least 50%, at least 60%, at least 70%, at least 80% or at least 90% of the infectivity compared to the infectivity of the starting material.

Stability of the adenoviral vectors can, amongst other methods, be determined by measuring the infectivity of the vector, e.g. retention of infectivity upon manipulation (e.g. freeze drying) or storage of the viral vector. The term "infectivity" refers to the ability of the vector to enter in a susceptible host, i.e. cells, and deliver its genetic material for expression by the host. Infectivity can be expressed as "the 50% cell culture infectious dose" (CCID50), which is the amount of adenoviral vector that is required to infect 50% of the cells in a given cell culture. Infectivity can be measured by measuring the proportion of cells wherein an adenoviral transgene is expressed. For example, green fluorescent protein can be used as infectivity marker whereby the number of cells expressing green fluorescent protein after 24 hours of incubation with the vector is determined. Alternatively, infectivity can be measured by determination of the number of cells expressing the adenovirus hexon capsid protein after 24 hours of incubation with the vector.

Adenovirus has been widely used for gene transfer applications due to its ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorised into six subgenera (A-F; B is subdivided into B1 and B2) according to sequence homology and on their ability to agglutinate red blood cells (Tatsis and Ertl, *Molecular Therapy* (2004) 10:616-629).

In one embodiment, the adenoviral vector of the present invention is derived from a human adenovirus. Examples of such human-derived adenoviruses are Ad1, Ad2, Ad4, Ad5, Ad6, Ad11, Ad 24, Ad34, Ad35, particularly Ad5, Ad11 and Ad35. Although Ad5-based vectors have been used extensively in a number of gene therapy trials, there may be limitations on the use of Ad5 and other human group C adenoviral vectors due to preexisting immunity in the general population due to natural infection. Ad5 and other human group C members tend to be among the most seroprevalent serotypes. Additionally, immunity to existing vectors may develop as a result of exposure to the vector during treatment. These types of preexisting or developed immunity to seroprevalent vectors may limit the effectiveness of gene therapy or vaccination efforts. Alternative adenovirus serotypes, thus constitute very important targets in the pursuit of gene delivery systems capable of evading the host immune response.

Therefore, in another embodiment, the adenoviral vector of the present invention is derived from a nonhuman simian adenovirus, also referred to simply as a simian adenovirus. Numerous adenoviruses have been isolated from nonhuman simians such as chimpanzees, bonobos, rhesus macaques and gorillas, and vectors derived from these adenoviruses induce strong immune responses to transgenes encoded by these vectors (Colloca et al. (2012) *Sci. Transl. Med.* 4:1-9; Roy et al. (2004) *Virol.* 324: 361-372; Roy et al. (2010) *J. Gene Med.* 13:17-25). Certain advantages of vectors based on nonhuman simian adenoviruses include the relative lack of cross-neutralising antibodies to these adenoviruses in the target population. For example, cross-reaction of certain chimpanzee adenoviruses with preexisting neutralizing antibody responses is only present in 2% of the target population compared with 35% in the case of certain candidate human adenovirus vectors.

In specific embodiments, the adenoviral vector is derived from a non-human adenovirus, such as a simian adenovirus and in particular a chimpanzee adenovirus such as ChAd3, ChAd63, ChAd83, ChAd155, ChAd157, Pan 5, Pan 6, Pan 7 (also referred to as C7) or Pan 9. Examples of such strains are described in WO03/000283, WO2010/086189 and GB1510357.5 and are also available from the American Type Culture Collection, 10801 University Boulevard, Manassas, Va. 20110-2209, and other sources. Alternatively, adenoviral vectors may be derived from nonhuman simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl, *Molecular Therapy* (2004) 10:616-629). Penton is another adenoviral capsid protein that forms a pentameric base to which fiber attaches. The trimeric fiber protein protrudes from the penton base at each of the 12 vertices of the capsid and is a knobbed rod-like structure. The primary role of the fiber protein is the tethering of the viral capsid to the cell surface via the interaction of the knob region with a cellular receptor, and variations in the flexible shaft as well as knob regions of fiber are characteristic of the different serotypes (Nicklin et al *Molecular Therapy* 2005 12:384-393).

Adenoviral vectors may be used to deliver desired RNA or protein sequences, for example heterologous sequences, for in vivo expression. A vector may include any genetic element including naked DNA, a phage, transposon, cosmid, episome, plasmid, or a virus. By "expression cassette" (or "minigene") is meant the combination of a selected heterologous gene (transgene) and the other regulatory elements necessary to drive translation, transcription and/or expression of the gene product in a host cell.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of the promoter of choice, cDNA sequence of the gene of interest and a poly A signal, resulting in a replication defective recombinant virus.

In one embodiment, the transgene encoded by the adenoviral vector is a sequence encoding a product which is useful in biology and medicine, such as therapeutic or immunogenic proteins, RNA, enzymes, or catalytic RNAs. Desirable RNA molecules include tRNA, dsRNA, ribosomal RNA, catalytic RNAs, RNA aptamers, and antisense RNAs. One example of a useful RNA sequence is a sequence which extinguishes expression of a targeted nucleic acid sequence in the treated animal.

Thus in one embodiment, the mixture or composition as described herein is for use in prophylactic (thus immunogenic or preventive) or therapeutic treatment of a subject, such as a mammal or human subject, depending on the transgene encoded by the adenoviral vector.

The transgene may encode a polypeptide or protein used for treatment, e.g., of genetic deficiencies, as a cancer therapeutic or vaccine, for induction of an immune response, and/or for prophylactic vaccine purposes. As used herein, induction of an immune response refers to the ability of a protein, also known as an "antigen" or "immunogen", to induce a T cell and/or a humoral immune response to the protein.

Immunogens expressed by the adenoviral vectors formulated as described herein and which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families.

In one embodiment, the immunogen is from a filovirus, for example Ebola (Zaire, Sudan, Reston, Budibugyo and Ivory Coast species) or Marburg. Such antigens may be derived from the viral glycoprotein (transmembrane and/or secreted form) and/or the viral nucleoprotein. Examples of such vectors can be found, inter alia, in WO2011/130627.

In another embodiment, immunogens may be selected from respiratory viruses such as respiratory syncytial virus (RSV) and other paramyxoviruses such as human metapneumovirus, hMPV and parainfluenza viruses (PIV). Suitable antigens of RSV which are useful as immunogens to immunize a human or non-human animal can be selected from: the fusion protein (F), the attachment protein (G), the matrix protein (M2) and the nucleoprotein (N). Such vectors are described in WO2012/089833 and PCT/EP2016/063297. In one embodiment, the ChAd155-RSV construct as disclosed in PCT/EP2016/063297 is considered for the compositions and methods disclosed.

In another embodiment, the immunogen may be from a retrovirus, for example a lentivirus such as the Human Immunodeficiency Virus (HIV). In such an embodiment, immunogens may be derived from HIV-1 or HIV-2 sequences, such as for Gag, Pol, Nef, Env, and others. Such vectors are described, inter alia, in GB1510357.5 and WO2008/107370.

In another embodiment, the immunogen may be from Human Papilloma Virus (HPV). In such an embodiment, immunogens may be derived from any HPV type and in particular from HPV types known to cause illness or disease, e.g. high risk HPV types causing urogenital cancers HPV16, HPV18 and the like.

Alternatively or in addition, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In addition to the transgene, the expression cassette also may include conventional control elements which are operably linked to the transgene in a manner that permits its transcription, translation and/or expression in a cell transfected with the adenoviral vector. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Adenoviral vectors are generated by the modification of the wild type adenovirus to express heterologous genes (transgenes) and/or delete or inactivate undesirable adenoviral sequences.

Adenoviral vectors may also have altered replication competency. For example the vector may be replication defective or have limited replication such that it has a reduced ability to replicate in non-complementing cells, compared to the wild type virus. This may be brought about by mutating the virus e.g. by deleting a gene involved in replication, for example deletion of the E1a, E1b, E3 or E4 gene. Such modifications are known to the skilled person and described in the art, e.g. by Roy et al., *Human Gene Therapy* 15:519-530, 2004; Colloca et al. (2012) *Sci. Transl. Med.* 4:1-9; Roy et al. (2004) *Virol.* 324: 361-372; or WO 03/000283.

These vectors are generated using techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence. Particularly suitable methods include standard homologous recombination methods such as those provided in Colloca et al. (2012) *Sci. Transl. Med.* 4:1-9; Roy et al. (2004) *Virol.* 324: 361-372; Roy et al. (2010) *J. Gene Med.* 13:17-25; and WO2010/085984 or recombineering methods as described in Warming et al. *Nuc. Acids Res.* (2005) 33:e36.

The adenoviral vectors can be produced on any suitable cell line in which the virus is capable of replication. In particular, complementing cell lines which provide the factors missing from the viral vector that result in its impaired replication characteristics (such as E1) can be used. Without limitation, such a cell line may be HeLa (ATCC Accession No. CCL 2), A549 (ATCC Accession No. CCL 185), HEK 293, KB (CCL 17), Detroit (e.g., Detroit 510, CCL 72) and WI-38 (CCL 75) cells, among others. These cell lines are all available from the American Type Culture Collection, 10801

University Boulevard, Manassas, Va. 20110-2209. Other suitable parent cell lines may be obtained from other sources, such as PER.C6™ cells, as represented by the cells deposited under ECACC no. 96022940 at the European Collection of Animal Cell Cultures (ECACC) at the Centre for Applied Microbiology and Research (CAMR, UK) or Her 96 cells (Crucell).

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. *PLOS One* (2013) 8(e55435):1-9). Procell92.S is adapted for growth in suspension conditions and is also useful for producing adenoviral vectors expressing toxic proteins (www.okairos.com/e/inner-s.php?m=00084, last accessed 13 Apr. 2015).

Adenoviral Delivery Methods and Dosage

A mixture or composition as described herein may comprise one or more recombinant vectors capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

Thus in one embodiment, the mixture and/or composition described herein are for use in immunization of a subject, such as a human subject. The levels of immunity of the selected gene can be monitored to determine the need, if any, for boosters. Following an assessment of antibody titers in the serum, optional booster immunizations may be desired.

In one embodiment, the aqueous mixture and/or (freeze-dried) compositions described herein may be administered to a mammal, e.g. to a human subject. In particular, those mixtures or compositions comprising adenoviral vector encoding a transgene (i.e. a recombinant adenoviral vector) that is a therapeutic or immunogenic protein are considered for formulation in the aqueous mixture or freeze-dried compositions described herein.

Optionally, a mixture or composition of the invention may be formulated to contain other components, including, e.g., further immunogen(s), e.g. polypeptide antigen(s), and/or adjuvants. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the adenoviral vectors of the invention.

In some embodiments, the mixture or composition as described herein is administered to a subject by intramuscular injection, intravaginal administration, intravenous injection, intraperitoneal injection, subcutaneous injection, epicutaneous administration, intradermal administration, nasal administration or oral administration.

If the therapeutic regimen involves co-administration of one or more adenoviral vectors and/or a further component, these may be coformulated (i.e. in the same mixture or composition) or each formulated in different compositions. When formulated separately, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1 \times 10^5$ to $1 \times 10^{15}$ viral particles, such as from $1 \times 10^8$ to $1 \times 10^{12}$ (e.g., $1 \times 10^8$, $5 \times 10^8$, $1 \times 10^9$, $5 \times 10^9$, $1 \times 10^{10}$, $2.5 \times 10^{10}$, $5 \times 10^{10}$, $1 \times 10^{11}$ $5 \times 10^{11}$, $1 \times 10^{12}$ particles). Alternatively, a viral vector can be administered at a dose that is typically from $1 \times 10^5$ to $1 \times 10^{10}$ plaque forming units (PFU), such as $1 \times 10^5$ PFU, $5 \times 10^5$ PFU, $1 \times 106$ PFU, $5 \times 10^6$ PFU, $1 \times 10^7$ PFU, $5 \times 10^7$ PFU, $1 \times 10^8$ PFU, $5 \times 10^8$ PFU, $1 \times 10^9$ PFU, $5 \times 10^9$ PFU, or $1 \times 10^{10}$ PFU. Dosages will vary depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be used. In another example, a suitable human or veterinary dosage may be in the range of about $1 \times 10^{11}$ to about $1 \times 10^{15}$ particles for an oral formulation.

The adenoviral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on A260 nm.

An immunologically effective amount of a nucleic acid may suitably be between 1 ng and 100 mg. For example, a suitable amount can be from 1 μg to 100 mg. An appropriate amount of the particular nucleic acid (e.g., vector) can readily be determined by those of skill in the art. Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg. Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be contained in a volume of between 0.3 ml and 2 ml. Thus the mixture and/or composition described herein can be formulated such that upon reconstitution of the dried composition a volume of, for example 0.3, 0.4, 0.5, 0.6, 1.0, 1.5 or 2.0 ml human dose per individual or combined immunogenic components is administered.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 µg to about 50 µg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the adenoviral vector may be delivered in a single administration or in various combination regimens, e.g., in combination with a regimen or course of treatment involving other active ingredients or in a prime-boost regimen.

Unless otherwise indicated, "therapy" or "therapeutic" may relate to either or both of preventive and curative therapy.

The aqueous mixture or dried composition may be contained in a glass vial, either siliconized or non-siliconized. In one embodiment, the aqueous mixture or dried composition are provided in a non-siliconized vial. Suitable, the aqueous mixture can be contained in a non-siliconized vial and freeze-dried when contained in that vial.

The invention also provides a kit comprising two containers, of which a first container comprises the adenoviral composition as defined herein and a second container comprises the liquid as defined herein for reconstitution of the dried composition.

The invention also provides a method for lyophilising or freeze-drying a liquid containing an adenoviral vector, such as the aqueous mixture as defined herein, to obtain a freeze-dried composition as defined herein, the method comprising an annealing step. Lyophilisation or freeze-drying cycle usually consists of three process phases.

In the first phase of the process, a mostly aqueous solution or mixture is frozen. Subsequently, water is removed first by sublimation during primary drying. In the third phase, non-frozen water is removed by diffusion and desorption during secondary drying. The inventors also found that the introduction of an annealing step during the freezing phase of the lyophilisation cycle has an unexpected positive impact on the stability of the adenoviral vector. Accordingly, the invention also provides a method for freeze-drying a liquid containing an adenoviral vector, such as the aqueous mixture as described herein, whereby the freezing step of the freeze-drying cycle comprises an annealing step.

Freezing and drying temperature and time will ultimately determine the moisture content of the freeze-dried composition. In an embodiment, the moisture content of the freeze-dried composition is 1.4% (w/w) or higher, e.g. between 1.4 and 10% (w/w), between 1.4 and 8% (w/w), between 1.7 and 8% (w/w), between 1.9 and 8% (w/w), between 1.4 and 5% (w/w), between 1.7 and 5% (w/w), between 1.9 and 5% (w/w), between 1.4 and 3% (w/w), between 1.7 and 3% (w/w), or between 1.9 and 3% (w/w). In a specific embodiment, the moisture content of the freeze-dried composition is 1.7% (w/w) or higher, 1.8% (w/w) or higher, or, 1.9% (w/w) or higher.

For the purpose of defining the method described the following terms are used as they are known in the art. The term "glass transition temperature" or "Tg" is the temperature at which an amorphous solid becomes soft upon heating or brittle upon cooling. The term "Tg'" refers to the glass transition temperature in the frozen state. The term "collapse temperature" or "Tc" refers to the temperature at which an amorphous material softens to the extent that it can no longer support its own structure. The terms "freeze-drying" and "lyophilising", and, "freeze-dried" and "lyophilised" are used interchangeably and refer to the same process of rapidly freezing a wet substance, followed by dehydration under reduced pressure.

The term "annealing step" as used herein, refers to a method step in freeze-drying cycles of a composition, wherein during the freezing phase the product is maintained at a specified subfreezing temperature for a predetermined period of time. As is known to the skilled person, annealing will lead to Oswald ripening of the ice crystals and cryoconcentration of the amorphous matrix. Typically, the annealing temperature is (slightly) above Tg'. In one embodiment, annealing is executed at a temperature between (Tg'+0.5° C.) and (Tg'+20° C.), e.g. at a temperature of −15° C.+/−9° C. or −15° C.+/−6° C., or between (Tg'+0.5° C.) and (Tg'+10° C.). In any case, the annealing temperature should be between Tg' and the melting temperature (Tm) during annealing. In specific embodiments, annealing is done at a temperature between −4° C. and −24° C., alternatively between −4° C. and −20° C., alternatively between −4° C. and −15° C., or alternatively between −8° C. and −15° C., e.g. at −10° C.+/−0.5° C. Annealing can be done during the freezing of the product, i.e. whilst the frozen sample is being formed, provided the product is frozen (solid state) and in a glassy state (below Tg'). Alternatively, annealing is done post freezing of the product.

In a specific embodiment, the annealing temperature is about −10° C. (e.g. −10° C.+/−1° C.), more in particular where the aqueous mixture comprises sorbitol and trehalose in a ratio of sorbitol to trehalose between 4/14 and 4/16.5.

In an embodiment, the product is frozen (i.e. product temperature below Tg') prior to the annealing step. In an embodiment, freezing is achieved by exposing the sample or aqueous mixture to a constant shelf temperature at a freezing temperature which is below Tg'. In an alternative embodiment, the product may be frozen by applying shelf-ramp freezing, i.e. gradually reducing the shelf temperature to a freezing temperature below Tg'. According to embodiments, the freezing temperature is a temperature below Tg' minus 5° C., below Tg' minus 7.5° C., or below Tg' minus 10° C., such as at or below −50° C. According to an embodiment, the product temperature (i.e. the temperature of the sample in the freeze-drier) at the time the freeze-drying cycle is started is between +2° C. and +8° C.

When applying shelf-ramp freezing, the temperature is reduced at a rate of at least 0.1° C./min, at least 0.2° C./min, at least 0.3° C./min or at least 0.5° C./min, and/or a rate of less than 10° C./min, 7.5° C./min, 5° C./min or less than 3° C./min. Alternatively, the temperature is reduced at a rate of 0.1 to 10° C./min, 0.1 to 5° C./min, 0.2 to 3° C./min, or 0.3 to 1° C./min. According to further embodiments, the shelf temperature reached is maintained for about or at least 1 hour (or 60 minutes).

In a further embodiment to the situation where the product is frozen before applying the annealing step, following the initial freezing of the sample or product, the shelf temperature is increased to a temperature above Tg' to initiate the annealing step, such as to a temperature above Tg' plus 0.5° C., above Tg' plus 1° C., above Tg' plus 3° C., above Tg' plus 5° C., above Tg' plus 10° C. or above Tg' plus 20° C. In any case, the temperature is kept below Tm during annealing. In an embodiment, the temperature is raised at a rate of at least 0.1° C./min, at least 0.2° C./min, at least 0.3° C./min or at least 0.5° C./min, and/or a rate of less than 10° C./min, 7.5°

C./min, 5° C./min or less than 3° C./min. Alternatively, the temperature is raised at a rate of 0.1 to 10° C./min, 0.1 to 5° C./min, 0.2 to 3° C./min, or 0.3 to 1° C./min. According to further embodiments, the annealing temperature is maintained for at least two and/or up to four hours.

In a further embodiment, following the annealing step, the shelf temperature is reduced to a temperature below Tg' prior to initiating the drying under reduced pressure, such as to a temperature below Tg' minus 5° C., below Tg' minus 7.5° C., or below Tg' minus 10° C., such as at or below −50° C. In an embodiment, to reach this, the temperature is reduced at a rate of at least 0.1° C./min, at least 0.2° C./min, at least 0.3° C./min or at least 0.5° C./min, and/or a rate of less than 10° C./min, less than 7.5° C./min, less than 5° C./min or less than 3° C./min. Alternatively, the temperature is reduced at a rate of 0.1 to 10° C./min, 0.1 to 5° C./min, 0.2 to 3° C./min, or 0.3 to 1° C./min. According to further embodiments, the shelf temperature reached is maintained for about or at least 1 hour (or 60 minutes).

Drying under reduced pressure as contemplated in step b.ii. of the lyophilisation method described herein will typically be done in two phases, i.e. primary drying and secondary drying. In an embodiment, step b.ii. of the method will include:
Step b.ii.1. for primary drying at a temperature below Tc of the product, and,
Step b.ii.2. for secondary drying at a temperature above Tc of the product and below the Tg of the product.

In specific embodiments, primary drying of the compositions described herein is done at −30° C.+/−5° C., secondary drying of the compositions described herein is done at 10° C.+/−5° C., or, primary drying of the compositions described herein is done at −30° C.+/−5° C. and secondary drying is done at 10° C.+/−5° C.

In specific embodiments, when freeze-drying compositions described herein, primary drying conditions are applied for 24 hours or longer, between 24 and 40 hours, or, between 30 and 40 hours.

In a further embodiment, primary drying is done at a pressure lower than 90 bar and/or above 40 µbar. Primary drying conditions may be applied for up to 24 hours or longer.

Another embodiment relates to the secondary drying temperature being achieved by raising the shelf temperature at a rate of 0.1° C./min, at least 0.2° C./min, at least 0.3° C./min or at least 0.5° C./min, and/or a rate of less than 3° C./min, less than 2° C./min, or less than 1° C./min. Alternatively, secondary drying temperature is achieved by raising the shelf temperature at a rate of 0.1 to 3° C./min, 0.2 to 2° C./min, or 0.3 to 1° C./min. According to yet another embodiment the secondary drying temperature is at least −10° C. and/or below 30° C. In a specific embodiment, the secondary drying temperature for the sorbitol containing compositions is 25° C.+/−5° C. In an alternative embodiment, when freeze-drying compositions described herein, secondary drying temperature is 10° C.+/−5° C.

Secondary drying conditions may be applied for at least or for about three hours, at least about four hours, at least about five hours, or, at least, or for about six hours.

Particular embodiments of the invention include:

Embodiment 1

A composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose and (viii) 3.5% (w/v) sorbitol.

Embodiment 2

A composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose and (vii) 23% (w/v) trehalose.

Embodiment 3

A composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) 0.02% (w/v) TWEEN 80.

Embodiment 4

A composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) 0.02% (w/v) TWEEN 80.

Embodiment 5

A lyophilised or freeze-dried composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose and (viii) 3.5% (w/v) sorbitol.

Embodiment 6

A lyophilised or freeze-dried composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose and (vii) 23% (w/v) trehalose.

Embodiment 7

A lyophilised or freeze-dried composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) 0.02% (w/v) TWEEN 80.

Embodiment 8

A lyophilised or freeze-dried composition comprising (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) 0.02% (w/v) TWEEN 80.

Embodiment 9

A composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose and (viii) 3.5% (w/v) sorbitol.

Embodiment 10

A composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose and (vii) 23% (w/v) trehalose.

Embodiment 11

A composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) 0.02% (w/v) TWEEN 80.

Embodiment 12

A composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) 0.02% (w/v) TWEEN 80.

Embodiment 13

A lyophilised or freeze-dried composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose and (viii) 3.5% (w/v) sorbitol.

Embodiment 14

A lyophilised or freeze-dried composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose and (vii) 23% (w/v) trehalose.

Embodiment 15

A lyophilised or freeze-dried composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) 0.02% (w/v) TWEEN 80.

Embodiment 16

A lyophilised or freeze-dried composition consisting essentially of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) 0.02% (w/v) TWEEN 80.

Embodiment 17

A composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) water for injection.

Embodiment 18

A composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) water for injection.

Embodiment 19

A composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol, (ix) 0.02% (w/v) TWEEN 80 and (ix) water for injection.

Embodiment 20

A composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose, (ix) 0.02% (w/v) TWEEN 80 and (ix) water for injection.

Embodiment 21

A lyophilised or freeze-dried composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose and (viii) 3.5% (w/v) sorbitol.

Embodiment 22

A lyophilised or freeze-dried composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose and (vii) 23% (w/v) trehalose.

Embodiment 23

A lyophilised or freeze-dried composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 18% (w/v) trehalose, (viii) 3.5% (w/v) sorbitol and (ix) 0.02% (w/v) TWEEN 80.

Embodiment 24

A lyophilised or freeze-dried composition consisting of (i) an adenoviral vector, (ii) 10 mM TRIS, (iii) 10 mM Histidine, (iv) 5 mM NaCl, (v) 1 mM MgCl$_2$, (vi) 2% (w/v) sucrose, (vii) 23% (w/v) trehalose and (ix) 0.02% (w/v) TWEEN 80.

Embodiment 25

The composition of any one of Embodiments 1 to 24 in which the adenoviral vector is a simian adenovector, such as a chimpanzee adenovector. Particularly an adenoviral vector selected from ChAd3, ChAd63, ChAd83, ChAd155, ChAd157, Pan 5, Pan 6, Pan 7 or Pan 9, yet more particularly an adenoviral vector is selected from ChAd3, ChAd63, ChAd83, ChAd155, ChAd157, and PanAd3 and still yet more particularly the adenoviral vector is ChAd155.

The present invention will now be further described by means of the following non-limiting examples.

EXAMPLES

Example 1—Evaluation of Sorbitol Effect and Comparison of Trehalose and Sucrose

The objectives of the experiment were to evaluate a protective effect of sorbitol on the adenovirus during freeze-drying, and to evaluate the impact of replacing the total trehalose load with sucrose. The ChAd155 vector used in the experiment encodes a respiratory syncytial viral protein (ChAd155-RSV) and is described in PCT/EP2016/063297. The ChAd155 particles were formulated in an aqueous mixture further comprising the excipients Tris 10 mM-Histidine 10 mM-MgCl2.6H2O 1 mM-Tween 80 0.02% (w/v)-NaCl 5 mM-Trehalose or Sucrose 23% (w/v)-Sorbitol 2% (w/v). Sugar concentration was calculated to reach the maximum osmolality allowed for paediatric injection, i.e. 900 mOsm/kg. The concentration of the viral particles was $1.1 \times 10^{11}$ pU/ml. This composition was calculated to be reached after the reconstitution of the freeze-dried material with 0.625 ml of water for injection in non-siliconized type glass vials filled with 0.5±0.02 ml. Then the vials were partially sealed with a Helvoet FM460 bromobutyl stopper inserted in freeze drying position (partially inserted to allow water vapor to escape during the freeze drying cycle).

The freeze-drying cycle used comprised the following steps (as shown in FIG. 1):
1. Freezing:
   The shelf temperature was set at −52° C. The filled vials were loaded into the freeze dryer when the shelf temperature was at or lower than −45° C. The samples were then cooled at −52° C. for a minimum of one hour.
2. Annealing step:
   The shelf temperature was raised to reach the target annealing temperature (−10° C.) in one hour
   The annealing temperature was maintained for two hours
   The shelf temperature was reduced again from −10° C. to −50° C. in the course of one hour.
   The product was maintained at −50° C. for at least one hour
3. Primary drying:
   The chamber pressure was set at 80 μbar and the shelf temperature was raised from −50° C. to −25° C. over three hours. Shelf temperature and chamber pressure were maintained for 24 hours.
4. Secondary drying:
   The shelf temperature was raised from −25° C. to +10° C. over six hours, whilst the chamber pressure was reduced at 40 μbar. When the shelf temperature reached +10° C., these conditions were maintained for six hours.

At the end of the freeze drying cycle, the chamber was filled with dry nitrogen until a chamber pressure of 825 mbar was reached, and then the stoppers were fully inserted into the vials (stoppering). Once stoppering was completed, the chamber pressure was equilibrated to atmospheric pressure for unloading. The chamber temperature was maintained at +2 to +8° C. until the vials were unloaded. The vials were then unloaded and over sealed with aluminium flip-off caps.

The results of this experiment are presented in the table below:

Two samples of purified-bulk ChAd155, diluted to reach the concentration of reconstituted vaccine, were used before and after treatment for 30 minutes at 60° C. as positive (fresh purified bulk control) and negative control (degraded purified bulk control) respectively.

The PicoGreen assay measures degradation of the viral particles. Quant-iT™ PicoGreen dsDNA reagent is an ultra-sensitive fluorescent nucleic acid stain for quantifying double stranded DNA in solution.

Infectivity HEXON of the adenoviral particles is measured by flow cytometric detection of cells stained for adenovirus hexon capsid protein. Adenovirus particle unit concentration is also measured using an Anion Exchange High Performance Liquid Chromatography (AEX-HPLC) system coupled with a fluorescence detector and using a commercial adenovirus standard as reference. The chromatographic systems used were Dionex Ultimate 3000 and Waters Acquity UPLC biocompatible (H-class).

Compositions containing trehalose showed an increase of the glass transition temperature inducing a better stability at high temperature storage of the product. Also, infectivity increased (10-20%) in the trehalose formulations compared to sucrose formulations.

Figure 3:
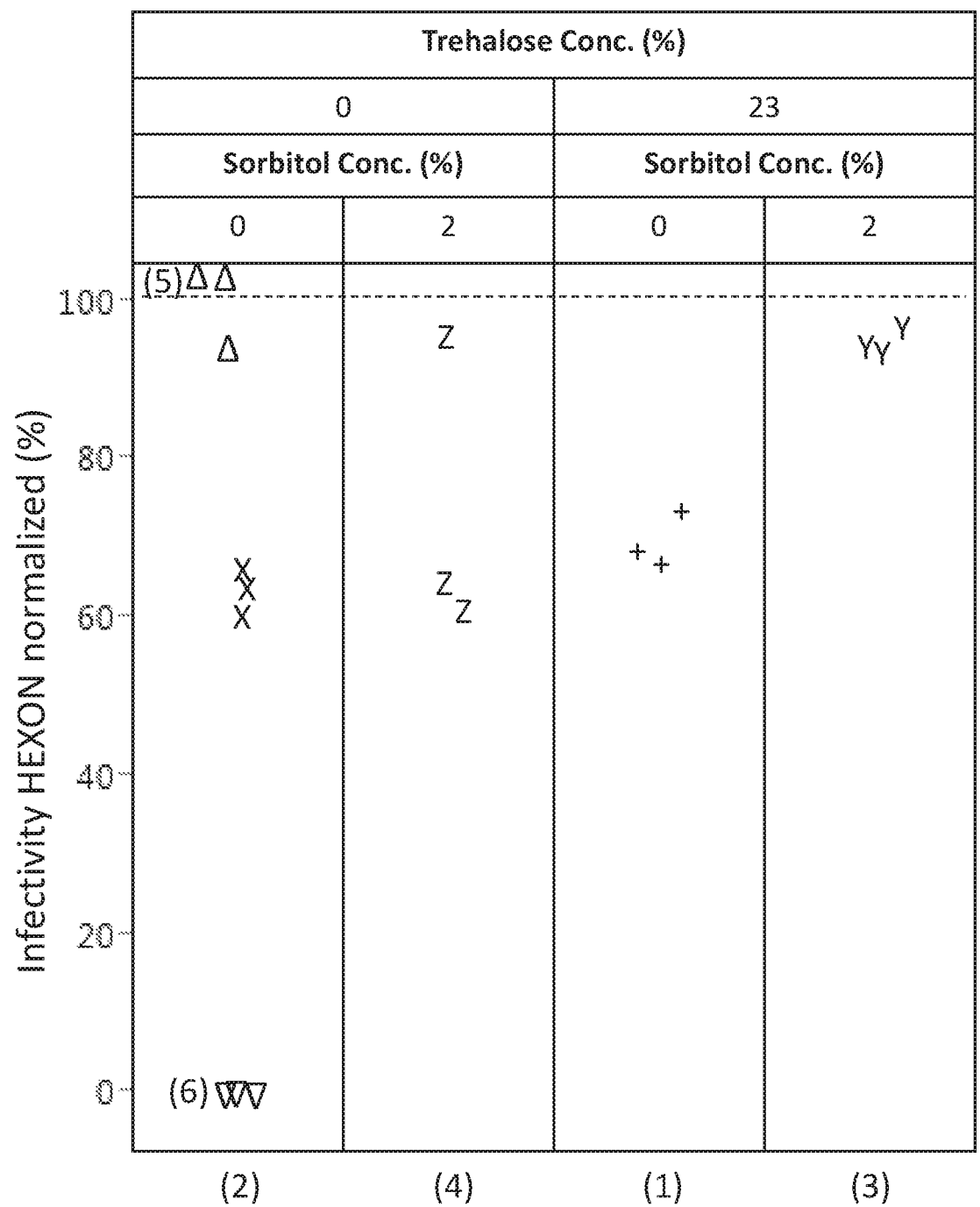
FIG. 3—infectivity of the adenoparticles contained in the compositions as obtained in Example 1: (1) trehalose 23% (designated by (+), (2) sucrose 23% (designated by X), (3) trehalose 23%+sorbitol 2% (designated by (Y), (4) sucrose 23%+sorbitol 2% (designated by (Z) and (5) Fresh purified bulk control (designated by upright triangle) and (6) degraded purified bulk control (designated by inverted triangle).

For the sorbitol containing formulations, it was noted that the presence of sorbitol lead to a decrease of the glass transition temperature (Tg), which could impact the appearance of the resulting cake. As illustrated in FIG. 3, the infectivity improved by 10-20% for compositions containing sorbitol.

Example 2—Determination of Statistical DOE for the Formulation Containing Trehalose, Sorbitol and NaCl The objective of the experiment was to evaluate several ranges of concentration of trehalose, sorbitol and NaCl to determine optimal conditions for the freeze-dried adenovirus candidate. The adenovirus used was ChAd155-RSV. The protective effect of trehalose and sorbitol as observed in Example 1 was further evaluated together with the impact of NaCl. The ChAd155-RSV particles were formulated in an aqueous mixture further comprising the excipients Tris 10 mM-Histidine 10 mM-MgCl2.6H2O 1 mM-Tween 80 0.02% (w/v)-NaCl (variable: 5, 25 or 45 mM)-Trehalose (14, 18.5 or 23% (v/w))-Sorbitol (0, 2 or 4% (v/w)). The concentration of the viral particles evaluated was $1.1 \times 10^1$ pU/ml. The compositions were calculated to be reached after reconstitution of the freeze-dried composition with 0.625 ml of water for injection in non-siliconized type glass vials filled with 0.5±0.02 ml. Then the vials were partially sealed with a Helvoet FM460 bromobutyl stopper inserted in freeze drying position (partially inserted to allow water vapor to escape during the freeze drying cycle).

The following compositions were tested:
sample 1: trehalose (T) 18.5% (v/w)-sorbitol (S) 0% (v/w)-NaCl (N) 25 mm
sample 2: T 14%-S 0%-N 5 mm
sample 3: T 18.5%-S 4%-N 25 mm

Figure 2:
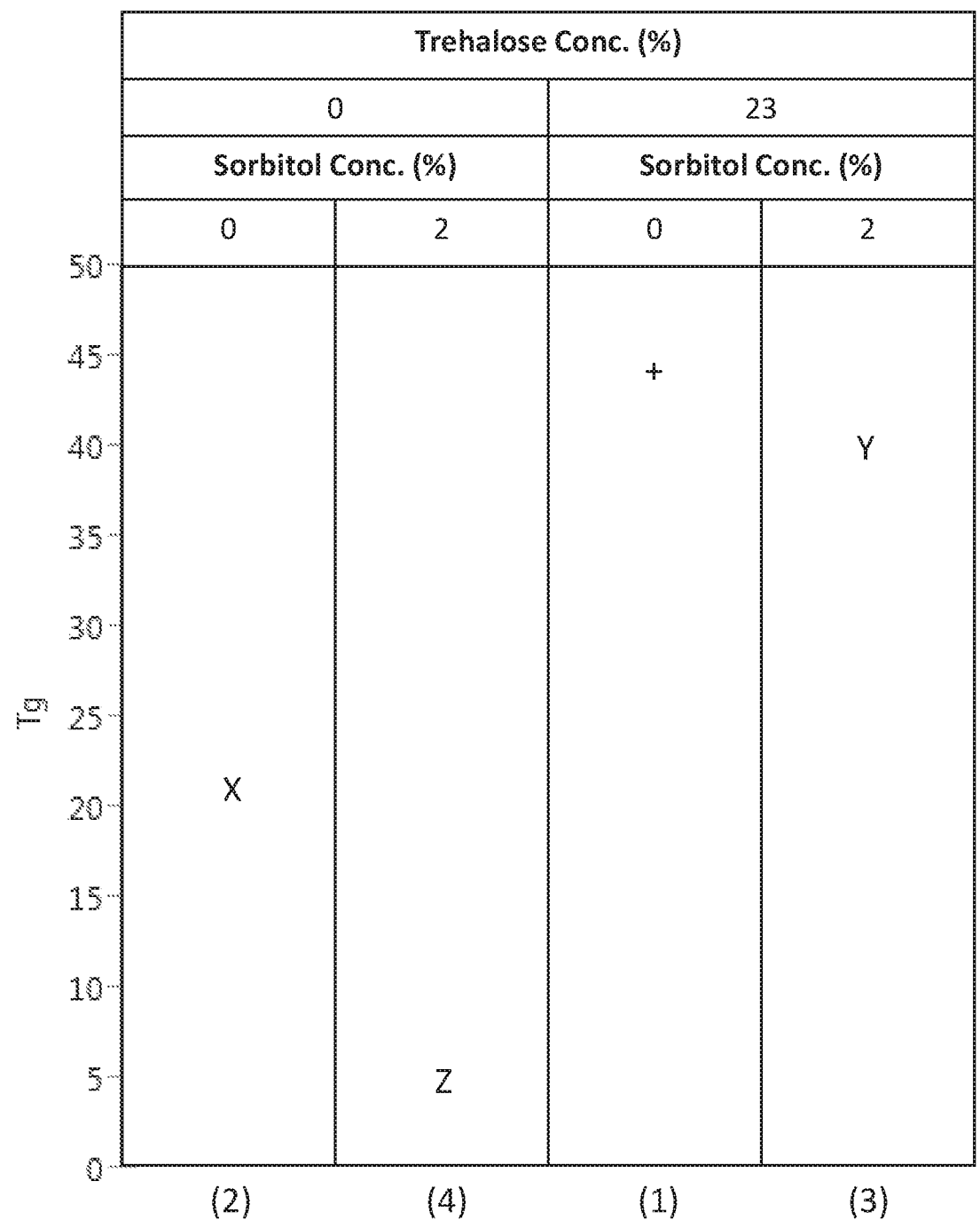
FIG. 2—glass transition temperatures (Tg) as determined for the composition tested in Example 1: (1) composition comprising trehalose 23%, (2) composition comprising sucrose 23%, (3) composition comprising trehalose 23%+sorbitol 2%, (4) composition comprising sucrose 23%+sorbitol 2%.

| | Sample description | Glass transition temperature (° C.) - (FIG. 2) | Residual humidity (%) | PicoGreen ® - free DNA (%) | Infectivity HEXON normalized (%) - (FIG. 3) | AEX-HPLC recovery (%) |
|---|---|---|---|---|---|---|
| 1 | Trehalose 23% | 44.4 | 3.2 | 5.3 | 72.1 | 71.3 |
| 2 | Sucrose 23% | 21.2 | 5.4 | 9.5 | 63.5 | 61.7 |
| 3 | Trehalose 23 + Sorbitol 2% | 40.0 | 4.2 | 3.6 | 94.3 | 77.0 |
| 4 | Sucrose 23% + Sorbitol 2% | 5.3 | 7.1 | 2.6 | 72.6 | 82.0 |
| 5 | Fresh purified bulk control | / | / | 0.0 | 100.0 | 102.9 |
| 6 | Degraded purified bulk control | / | / | 100.0 | 0.0 | 5.6 | sample 4: T 18.5%-S 2%-N 25 mm
sample 5: T 23%-S 0%-N 5 mm
sample 6: T 23%-S 4%-N 45 mm
sample 7: T 18.5%-S 2%-N 25 mm
sample 8: T 14%-S 4%-N 5 mm
sample 9: T 23%-S 0%-N 45 mm
sample 10: T 14%-S 2%-N 25 mm
sample 11: T 18.5%-S 2%-N 5 mm
sample 12: T 14%-S 0%-N 45 mm
sample 13: T 18.5%-S 2%-N 25 mm
sample 14: T 14%-S 4%-N 45 mm
sample 15: T 23%-S 2%-N 25 mm
sample 16: T 18.5%-S 2%-N 45 mm
sample 17: T 23%-S 4%-N 5 mm
sample 18: fresh purified bulk control
sample 19: degraded purified bulk control Two samples of purified-bulk ChAd155, diluted to reach the concentration of reconstituted vaccine, were used before and after treatment for 30 minutes at 60° C. as positive (fresh purified bulk control) and negative control (degraded purified bulk control) respectively.

Figure 4:
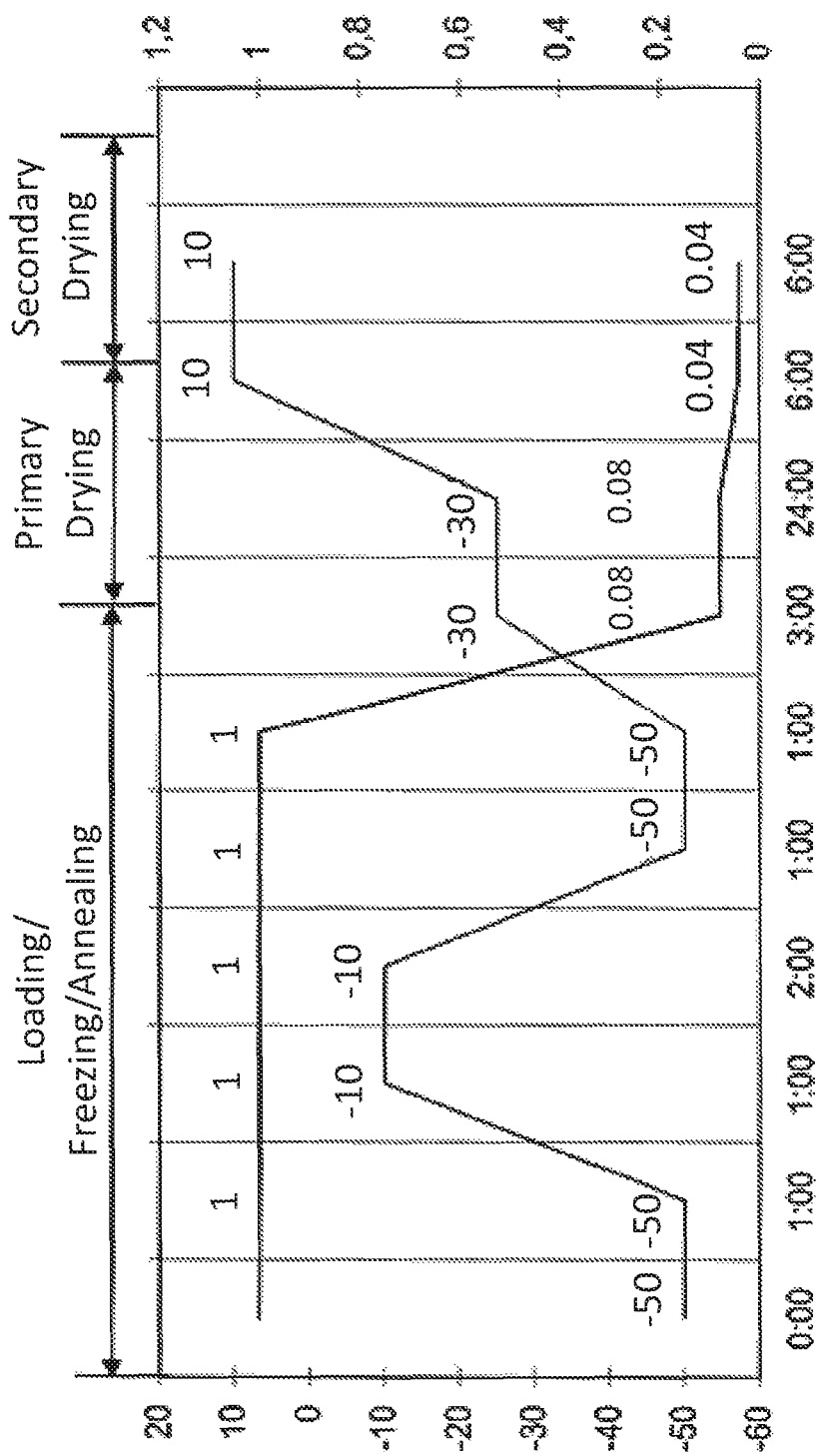
FIG. 4—illustration of freeze-drying cycle as used in Example 2.

The freeze-drying cycle used comprised the following steps (as shown in FIG. 4):

1. Freezing:
   The shelf temperature was set at −52° C. The filled vials were loaded into the freeze dryer when the shelf temperature was at or lower than −45° C. The samples were then cooled at −52° C. for a minimum of one hour
2. Annealing step:
   The shelf temperature was raised to reach the target annealing temperature (−10° C.) in one hour
   The annealing temperature was maintained for two hours
   The shelf temperature was reduced again from −10° C. to −50° C. in the course of one hour
   The product was maintained at −50° C. for at least one hour
3. Primary drying:
   The chamber pressure was set at 80 bar and the shelf temperature was raised from −50° C. to −30° C. over three hours. Shelf temperature and chamber pressure were maintained for 24 hours
4. Secondary drying:
   The shelf temperature was raised from −25° C. to +10° C. over six hours, whilst the chamber pressure was reduced at 40 bar. When the shelf temperature reached +10° C., these conditions were maintained for six hours At the end of the freeze drying cycle, the chamber was filled with dry nitrogen until a chamber pressure of 825 mbar was reached, and then the stoppers were fully inserted into the vials (stoppering). Once stoppering was completed, the chamber pressure was equilibrated to atmospheric pressure for unloading. The chamber temperature was maintained at +2 to +8° C. until the vials were unloaded. The vials were then unloaded and over sealed with aluminium flip-off caps.

All samples were analyzed at T0 and after storage for one week at +4° C., +25° C. (T1W25) or +30° C.

Figure 5:
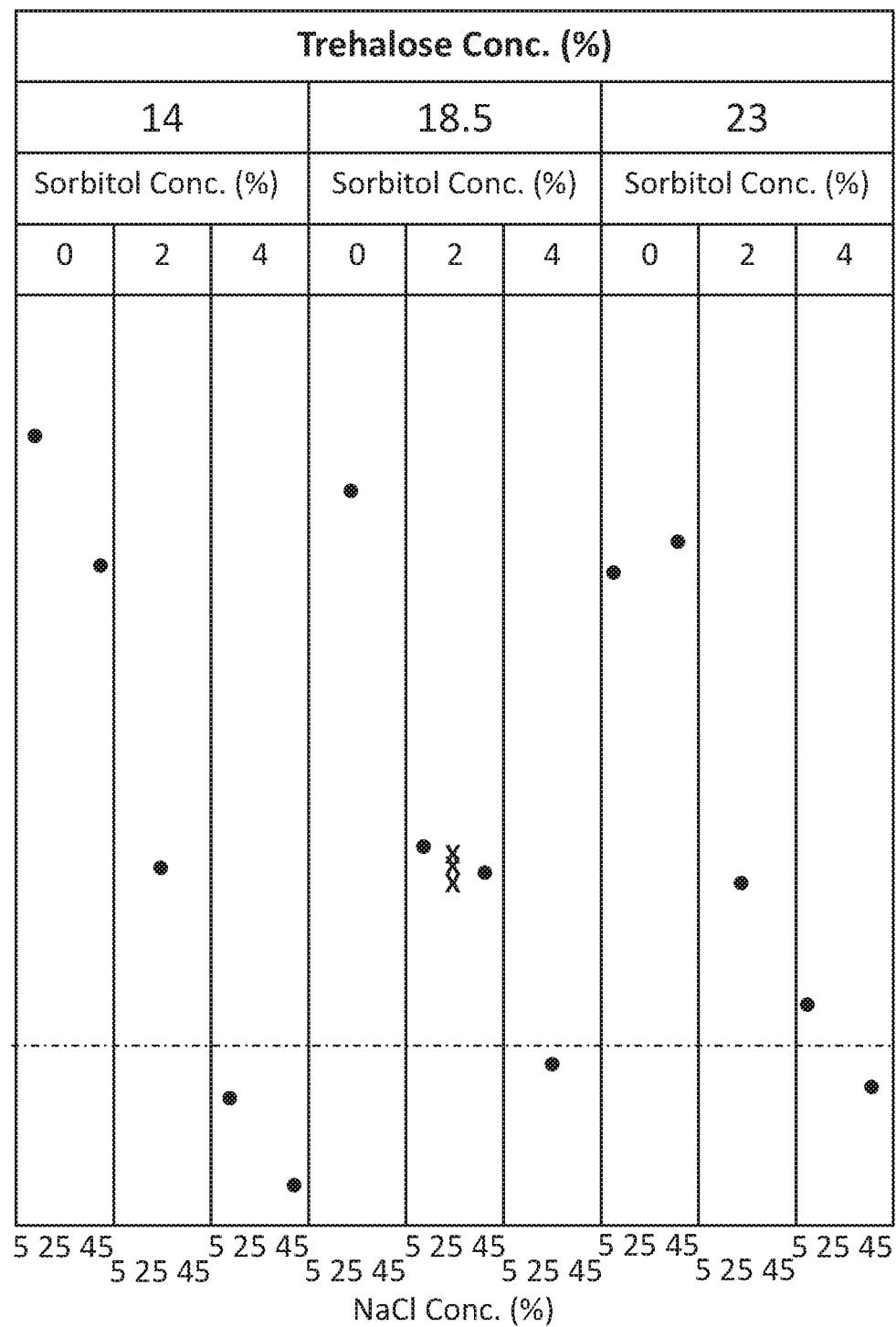
FIG. 5—Tg as determined in Example 2.
Figure 6:
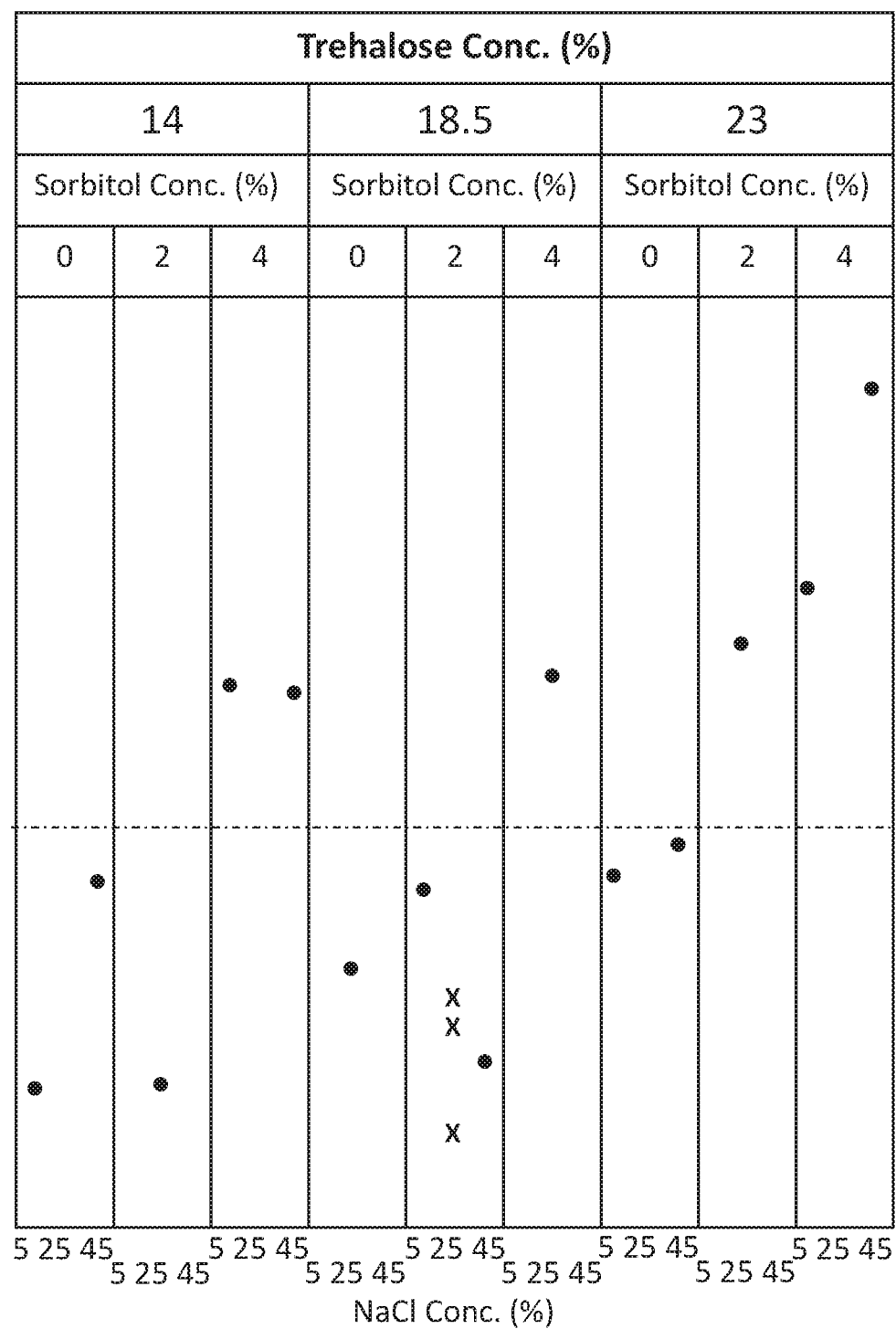
FIG. 6—moisture content as determined in Example 2.
Figure 7:
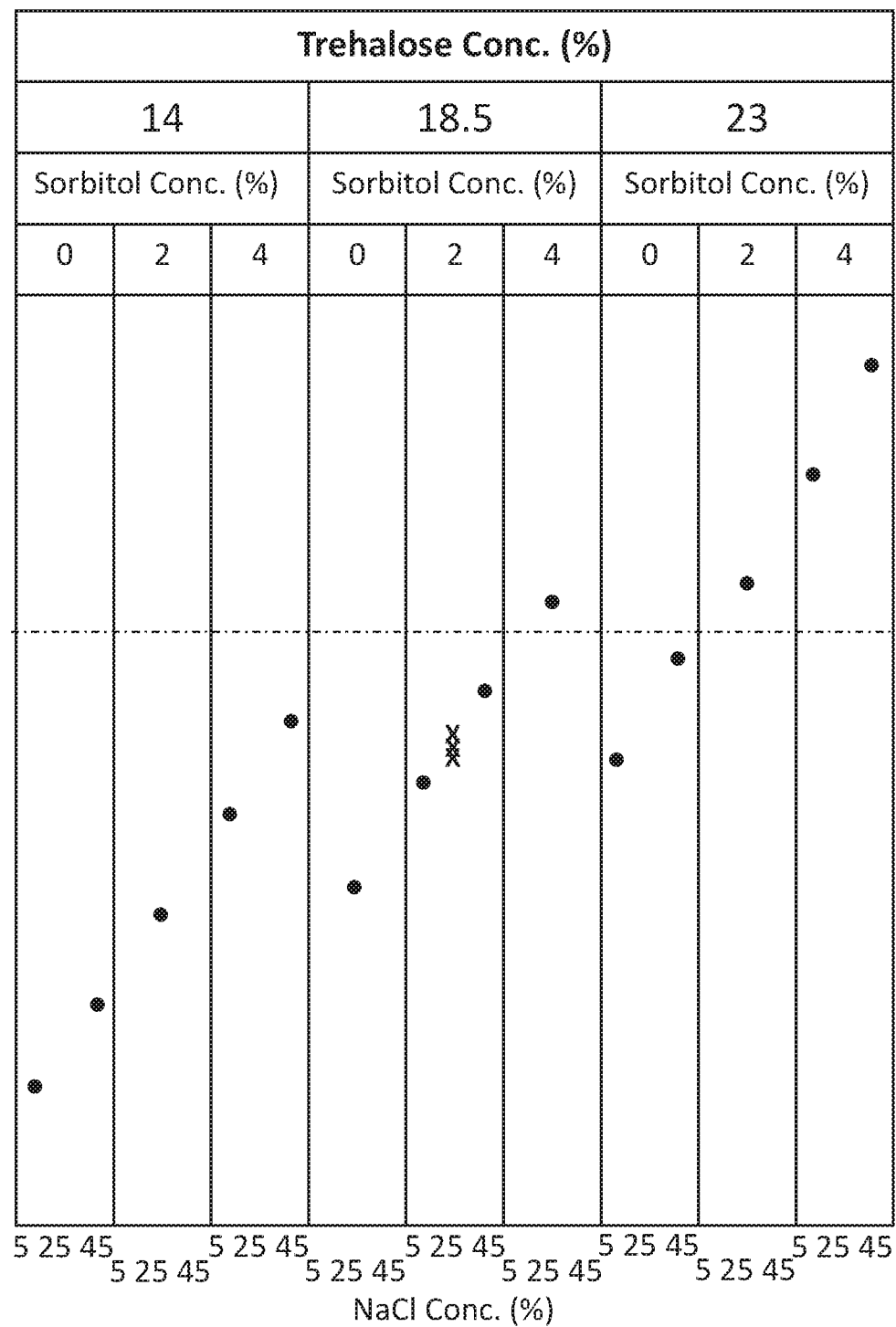
FIG. 7—osmolality as determined in Example 2.
Figure 8:
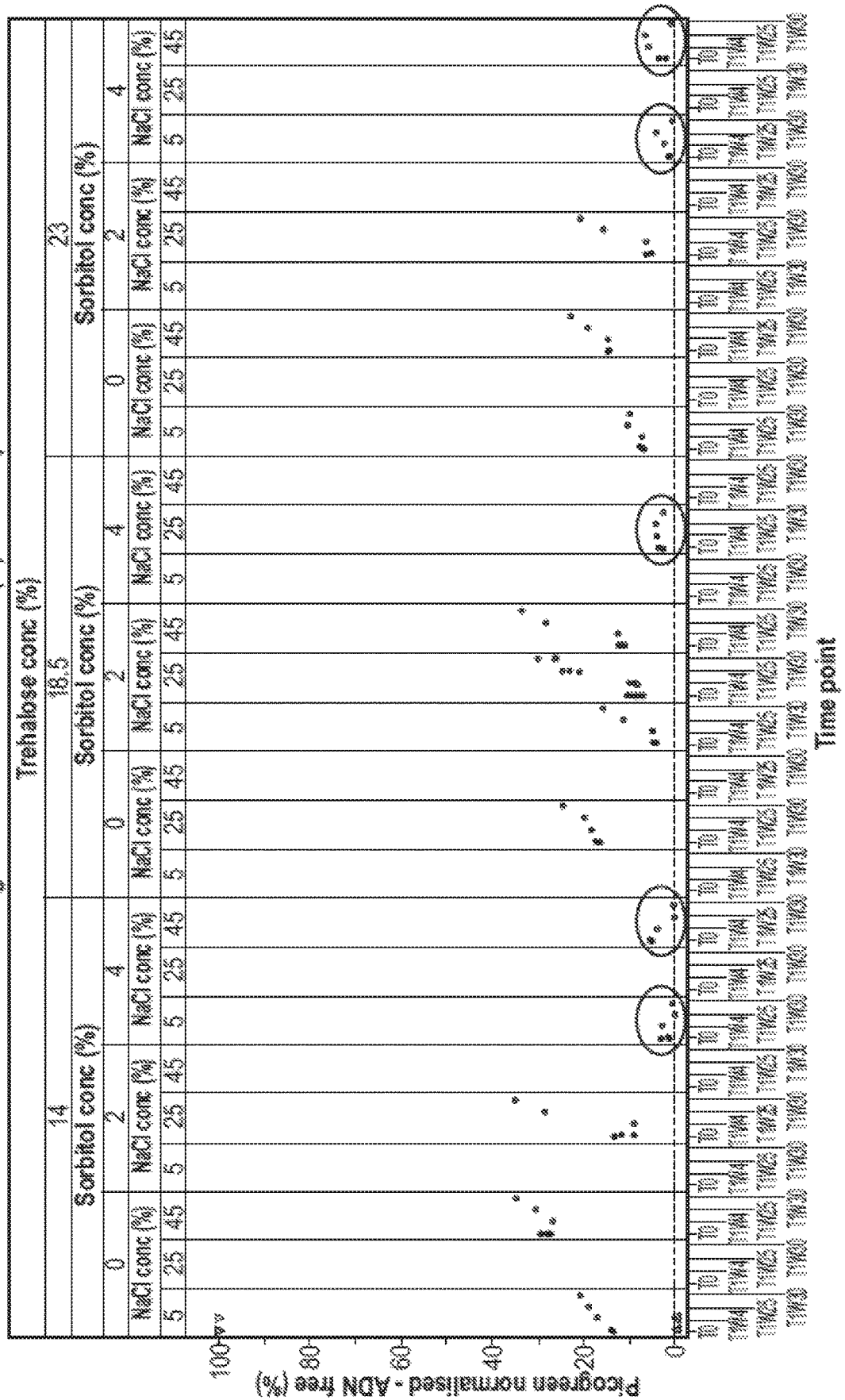
FIG. 8—PicoGreen data as determined in Example 2.
Figure 9:
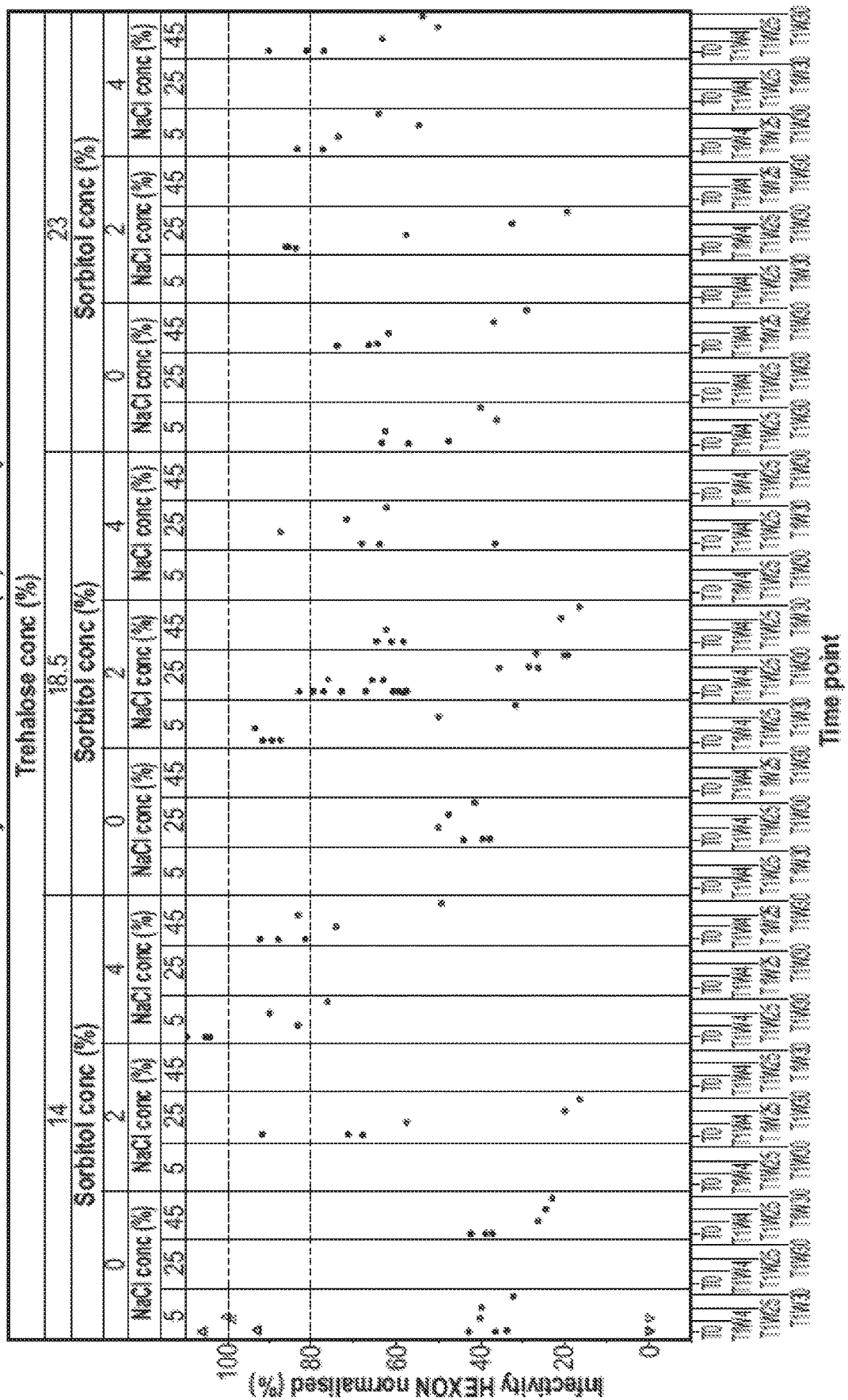
FIG. 9—infectivity as determined in Example 2.
Figure 10:
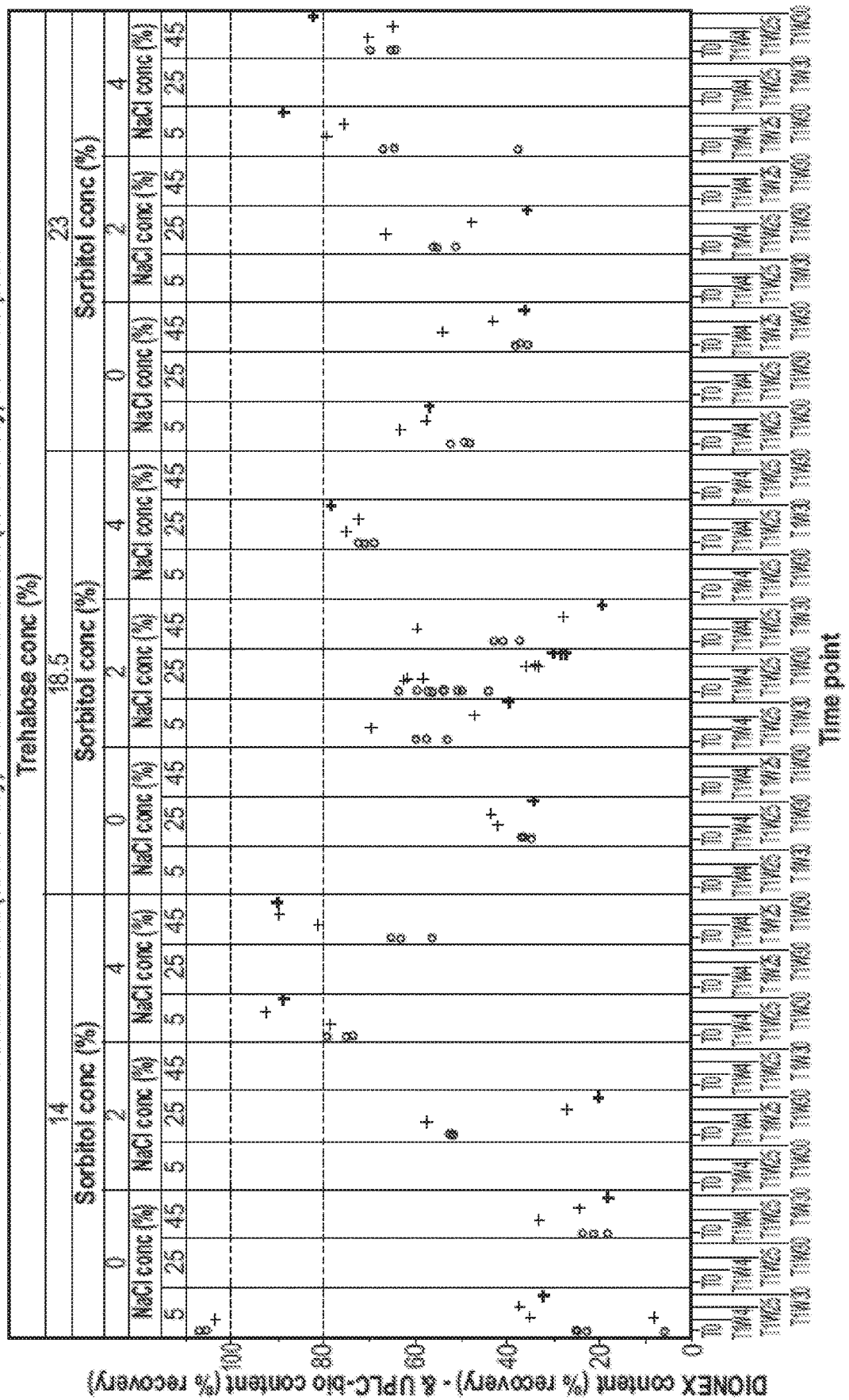
FIG. 10—ultra-performance liquid chromatography (UPLC) recovery as determined in Example 2.

The results of this experiment are presented in the table below:

| Time point | Glass transition temp. (° C.) (FIG. 5) T0 | Residual humidity (%) (FIG. 6) T0 | Osmolality (mOsm/kg) (FIG. 7) T0 | PicoGreen ® - free DNA (%) (FIG. 8) T0 | | Infectivity HEXON normalized (%) (FIG. 9) T0 | | AEX-HPLC recovery (%) (FIG. 10) T0 (by DIONEX) | T1W25 (by H-class) | qPCR (gE/ml) T0 |
|---|---|---|---|---|---|---|---|---|---|---|
| | | | | T0 | T1W25 | T0 | T1W25 | | | |
| 1 | 75.9 | 2.4 | 676 | 17.0 | 19.8 | 40.6 | 47.7 | 36.2 | 18.4 | $1.05 \times 10^{11}$ |
| 2 | 81.0 | 1.9 | 497 | 13.9 | 18.9 | 37.9 | 40.0 | 24.2 | 37.5 | $1.10 \times 10^{11}$ |
| 3 | 23.4 | 3.5 | 923 | 3.3 | 4.3 | 56.4 | 71.9 | 70.9 | 72.4 | $1.13 \times 10^{11}$ |
| 4 | 42.7 | 1.8 | 811 | 7.9 | 24.7 | 61.1 | 26.4 | 60.0 | 33.5 | $1.10 \times 10^{11}$ |
| 5 | 68.7 | 2.8 | 786 | 7.5 | 10.4 | 56.1 | 36.2 | 50.1 | 57.9 | $1.06 \times 10^{11}$ |
| 6 | 21.4 | 4.7 | 1131 | 3.2 | 6.5 | 83.0 | 50.2 | 66.6 | 65.2 | $1.14 \times 10^{11}$ |
| 7 | 41.4 | 2.2 | 801 | 8.8 | 21.1 | 64.5 | 35.7 | 55.2 | 36.0 | $1.14 \times 10^{11}$ |
| 8 | 20.1 | 3.5 | 737 | 2.0 | 0.1 | 106.6 | 90.1 | 76.0 | 92.7 | $1.20 \times 10^{11}$ |
| 9 | 71.2 | 2.9 | 876 | 14.7 | 19.1 | 68.4 | 36.9 | 37.0 | 43.2 | $9.89 \times 10^{10}$ |
| 10 | 41.4 | 2.0 | 650 | 11.5 | 28.6 | 77.3 | 20.1 | 52.2 | 27.2 | $1.13 \times 10^{11}$ |
| 11 | 43.2 | 2.7 | 764 | 4.4 | 11.3 | 89.6 | 50.0 | 57.0 | 47.5 | $1.12 \times 10^{11}$ |
| 12 | 69.0 | 2.7 | 573 | 28.3 | 30.7 | 39.7 | 24.7 | 21.2 | 24.4 | $1.10 \times 10^{11}$ |
| 13 | 42.2 | 2.3 | 795 | 8.9 | 23.1 | 80.2 | 28.7 | 48.4 | 34.2 | $1.01 \times 10^{11}$ |
| 14 | 11.7 | 3.5 | 816 | 5.2 | 0.1 | 87.5 | 83.3 | 61.8 | 89.7 | $9.99 \times 10^{10}$ |
| 15 | 39.9 | 3.7 | 941 | 5.6 | 15.7 | 85.4 | 32.7 | 54.3 | 47.8 | $1.03 \times 10^{11}$ |
| 16 | 41.1 | 2.0 | 847 | 12.0 | 28.5 | 61.6 | 21.2 | 40.5 | 27.8 | $9.26 \times 10^{10}$ |
| 17 | 28.7 | 3.9 | 1035 | 1.3 | 4.3 | 79.5 | 54.9 | 56.5 | 75.7 | $9.35 \times 10^{10}$ |
| 18 | / | / | / | 0.0 | | 100.0 | | 106.4 | 103.8 | $1.62 \times 10^{11}$ |
| 19 | / | / | / | 100.0 | | 0.0 | | 6.0 | 8.3 | $1.59 \times 10^{11}$ |

PicoGreen assay and infectivity HEXON were as described for Example 1. Quantitative PCR (qPCR) as reported herein allows one to determine the virus content. The test targets the hCMV promoter present in the adenovirus. The DNA sample was extracted with Quiagen QIAmp 96 DNA Blood. Results are expressed as genome equivalents per milliliter (gE/ml). The best results taking the overall parameters into account (e.g. PicoGreen value at the lowest, infectivity and HPLC content at the highest, osmolality lower than 900 mOsm/kg), were achieved with compositions comprising 14 to 18.5% trehalose, 4% sorbitol and NaCl<25 mm.

Figure 11:
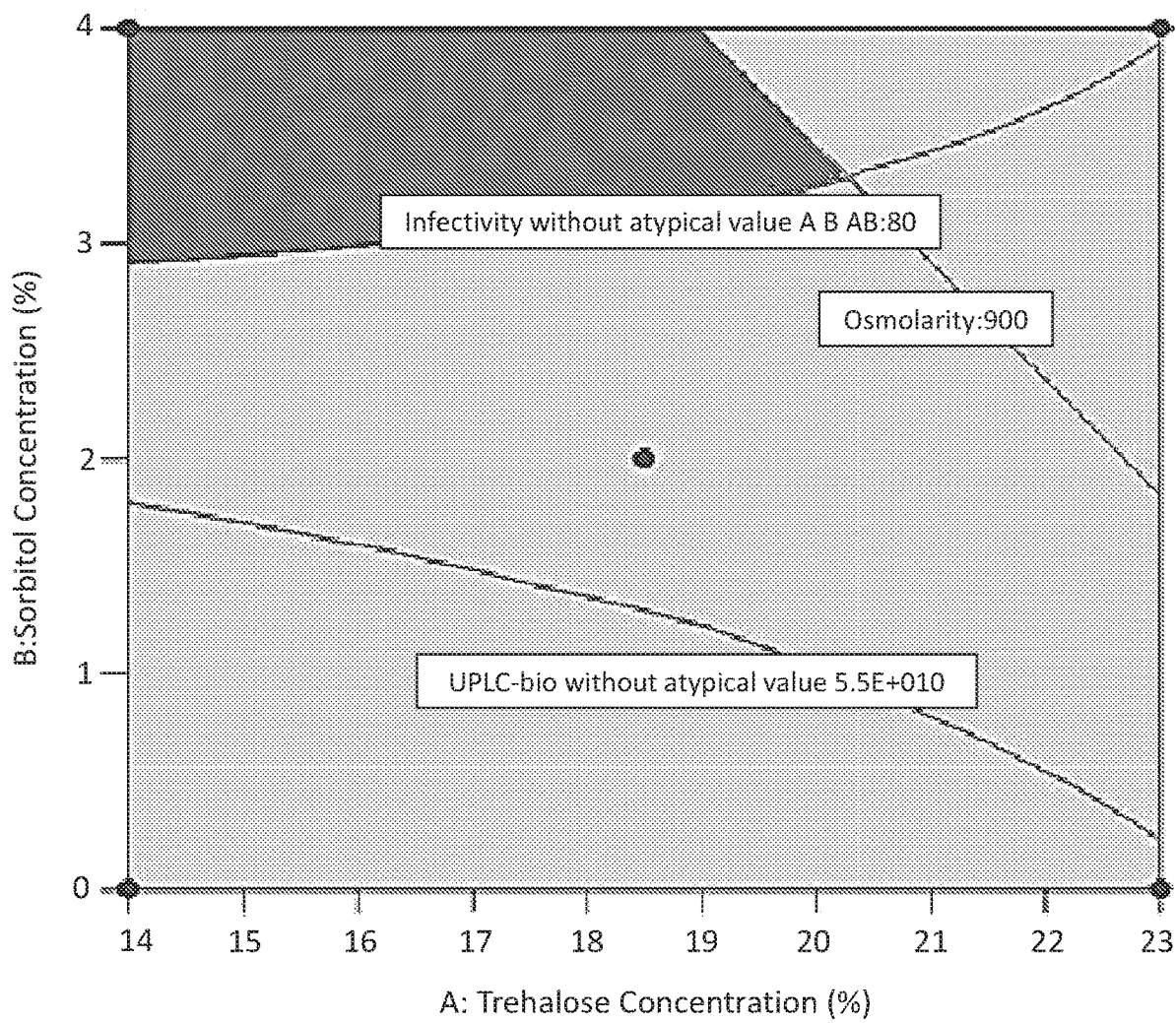
FIG. 11—illustration of the statistical analysis of data with respect to different parameters as determined in Example 2 to identify optimized combinations (design of experiments (DOE) plot 1).

Following a statistical analysis the following optimised compositions were identified based on different constraints sets of parameters (see FIG. 11 for Design of Experiments (DOE) plot 1):
  Not taking into account constraints with respect to Tg, the best candidate would be Trehalose=14%/Sorbitol=4%/NaCl=5 mM.

Taking into account that the Tg should be >25° C., the best candidates would be Trehalose=14%-16%/Sorbitol=3%/NaCl=5 mM.

Figure 12:
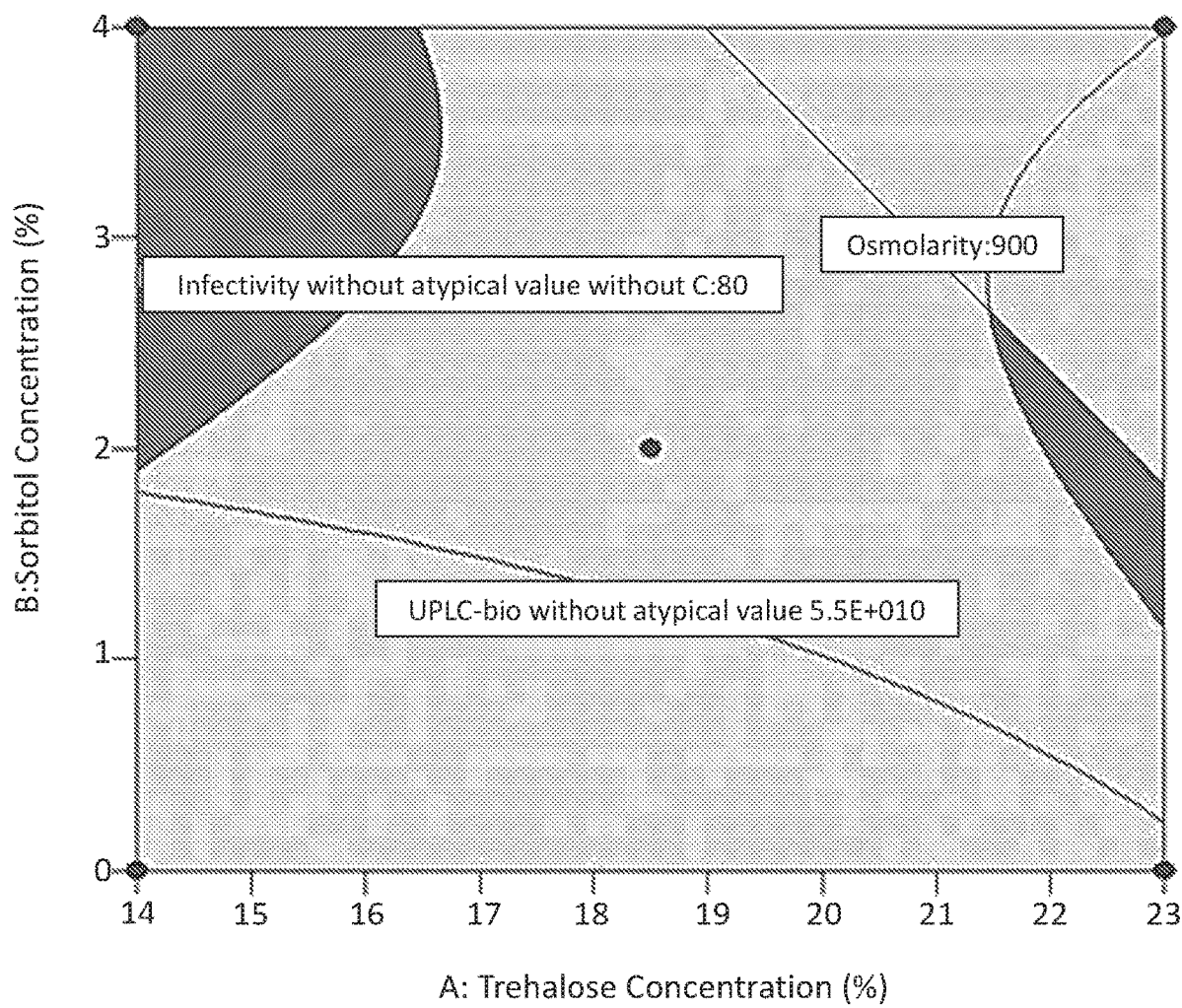
FIG. 12—illustration of the statistical analysis of data with respect to different parameters as determined in Example 2 to identify optimized combinations wherein higher trehalose concentrations are allowed (DOE plot 2).

For compositions where higher trehalose content is desirable, the following optimized compositions were identified (see FIG. 12 for DOE plot 2):

trehalose=22%, sorbitol=2% and NaCl=5 mM.

The effect of the sorbitol content on the Tg of the freeze-dried composition impacted the appearance of the resulting cake and the stability of the adenoviral particle stored therein. The decrease of the glass transition temperature of the candidates including sorbitol in their composition led to poor appearance of the cake (melting/collapse) upon one week at +25° C. and +30° C. It was observed that the reduced glass transition temperature was directly correlated with the moisture content (residual humidity) measured in the cake after the freeze-drying step. However, surprisingly, at the same time it was observed that samples with the higher moisture content (measured by Karl Fisher titration) better maintained infectivity of the adenoviral particle upon storage. Despite the melted appearance of the cakes, infectivity remained higher, provided a minimum moisture content was maintained of at least 1.8% w/w.

Example 3—Statistical DOE for the Formulation Trehalose/Sorbitol/NaCl

The results of Example 2 supported optimal ranges for trehalose (14-16%), Sorbitol (3-4%) and NaCl (5 mm).

Further compositions were tested to complement the data of Example 2 using the same ChAd155-RSV. For the compositions evaluated, the molarity of NaCl was fixed at 5 mm. Trehalose and sucrose content was varied as follows:

| Composition | Trehalose | Sucrose |
|---|---|---|
| 1 | 14% | 3% |
| 2 | 14% | 4% |
| 3 | 16% | 3% |
| 4 | 16% | 3.5% |
| 5 | 16% | 4% |
| 6 | 18% | 3% |
| 7 | 18% | 4% |
| 8* | 20% | 3.5% |

*resulting Osmolality of 910 mOsm/kg

Two samples of purified-bulk ChAd155 diluted to reach the concentration of reconstituted vaccine were used before and after treatment for 30 minutes at 60° C. as positive and negative controls respectively.

Also the freeze-drying cycle was evaluated in order to improve the stability of the cake appearance after storage (especially at +25° C. (room temperature) in order to cover the time for reconstitution and administration to the patient after storage at cold temperature).

Figure 13:
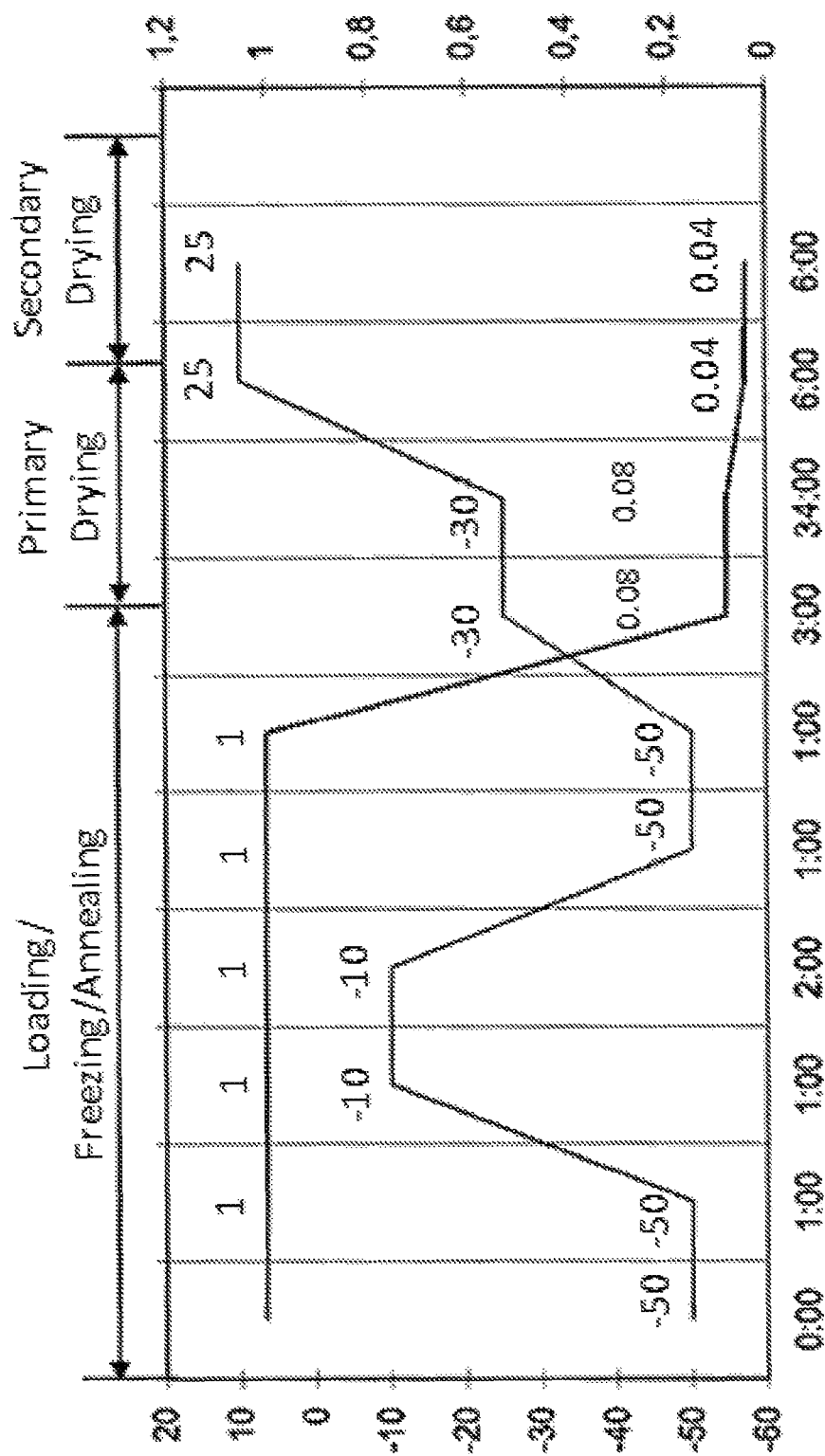
FIG. 13—freeze drying cycle 1 as used in Example 3.
Figure 14:
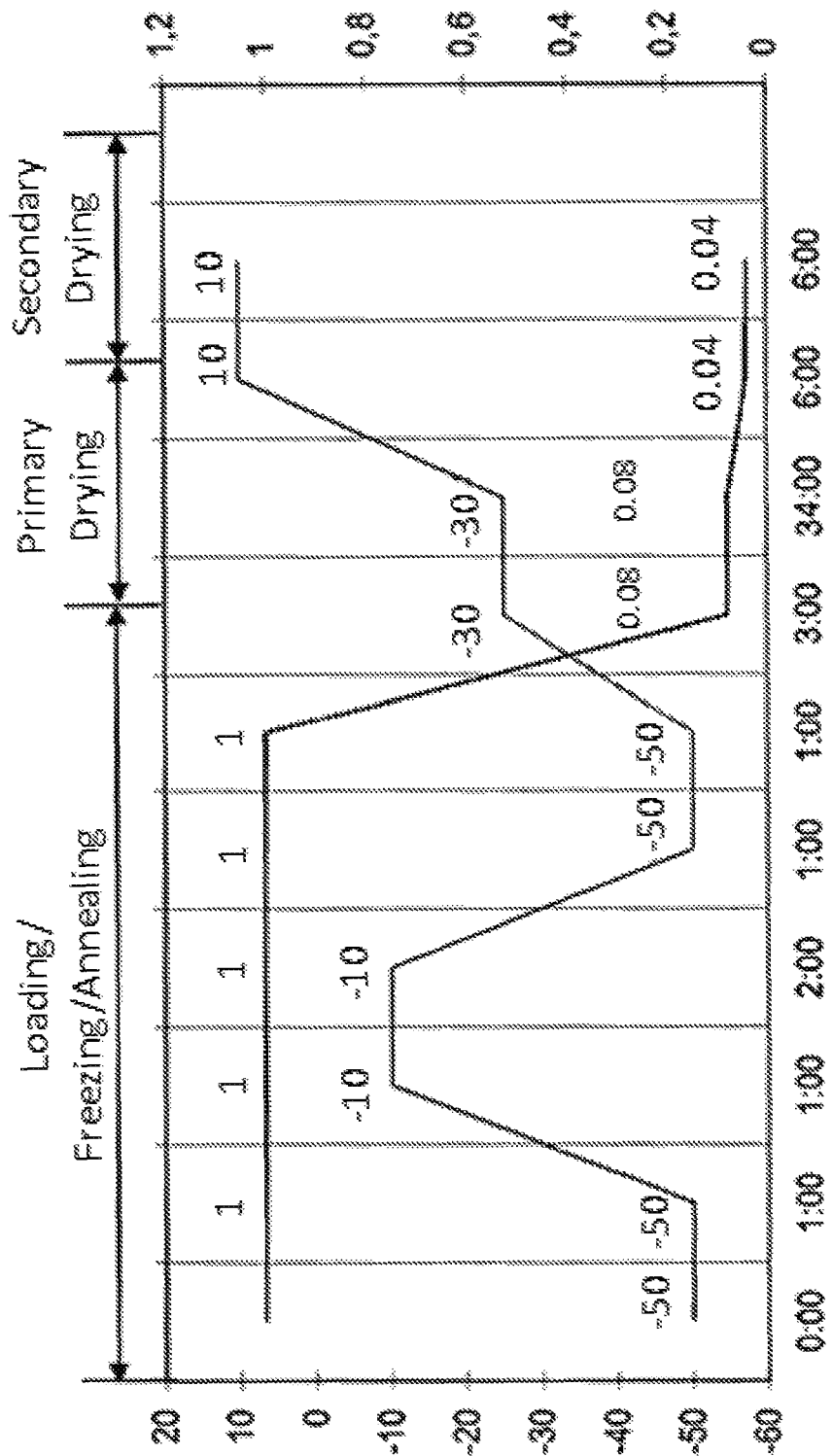
FIG. 14—freeze drying cycle 2 as used in Example 3.

In Example 2, the impact of decreased Tg in the presence of sorbitol was determined to be directly correlated with the moisture content (residual humidity) measured in the cake after the freeze-drying step. Although the data showed that the moisture content had a protective effect on the infectivity of adenovirus upon stability, poor appearance of the cakes (melted aspect) is undesirable. For that purpose, the freeze-drying or lyophilisation cycle was further optimized as follows:

lyo cycle (1): longer primary drying phase (+10H) was used in combination with a higher secondary drying temperature (at +25° C.) (see FIG. 13).

lyo cycle (2): longer primary drying phase (+10H) was used in combination with a secondary drying temperature of +10° C. (see FIG. 14).

The freeze-dried products were evaluated at T0 and after stability of one week at +4° C. (T1W4), +25° C. (T1W25) and +30° C. (T1W30).

Figure 15:
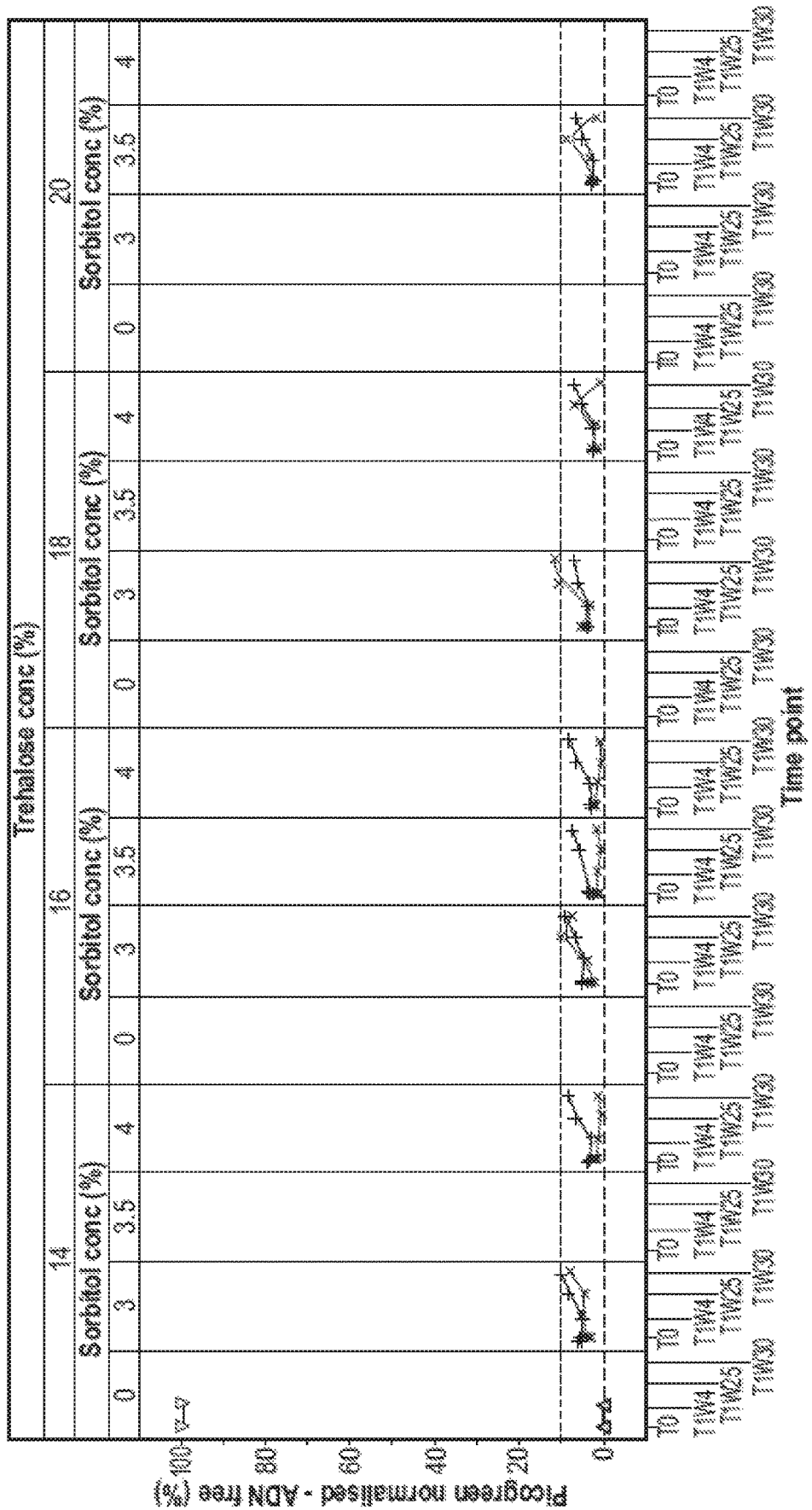
FIG. 15—PicoGreen data as determined in Example 3: (x) data points for samples obtained using freeze-drying condition with secondary desiccation at +10° C. (lyo cycle (2)), (+) data points for samples obtained using freeze-drying condition with secondary desiccation at +25° C. (lyo cycle (1)), (upright triangle)—control adenoviral stock, (inverted triangle)—negative control degraded adenoviral stock.
Figure 16:
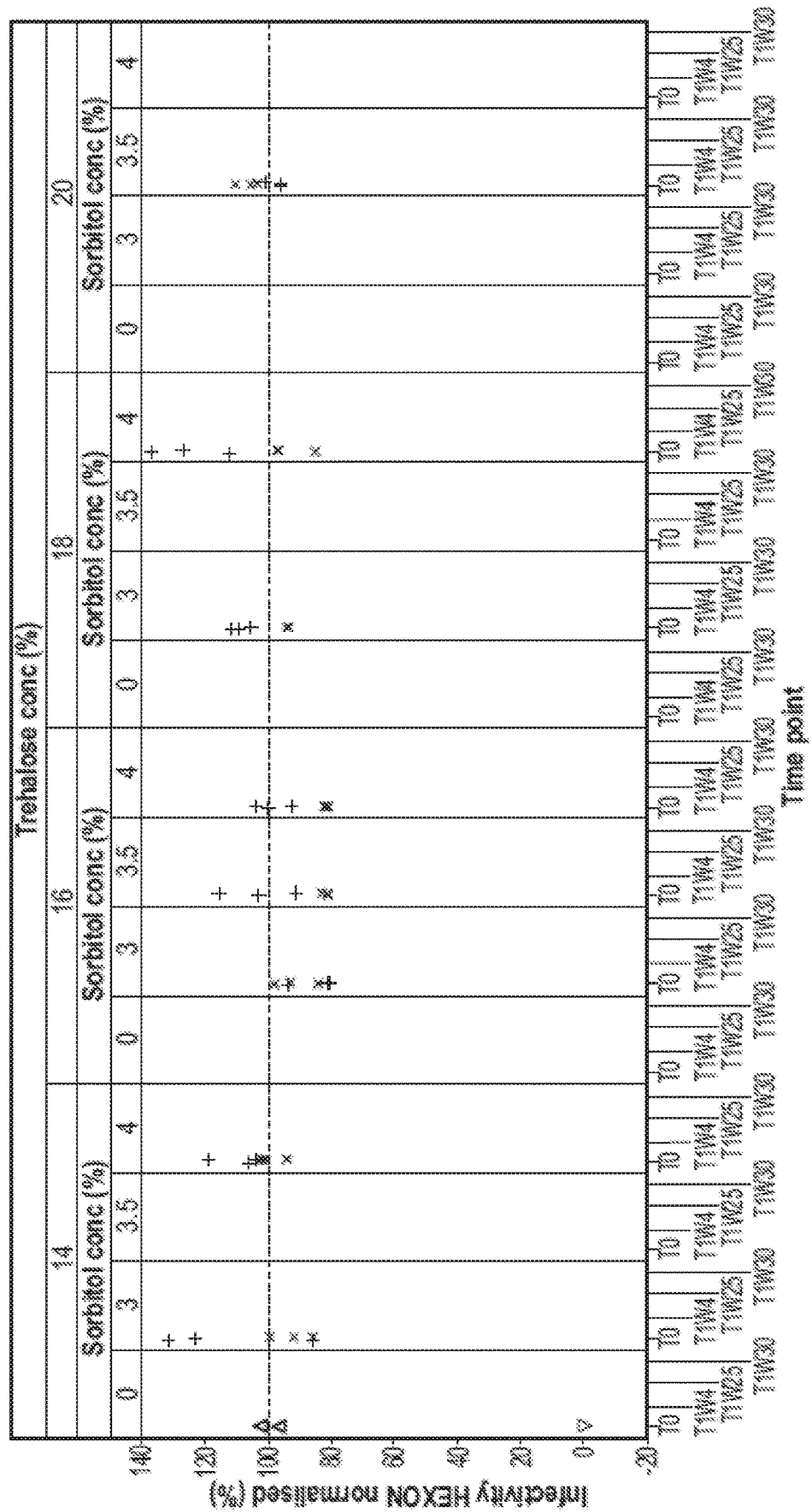
FIG. 16—infectivity data as determined in Example 3: (x) data points for samples obtained using a freeze-drying condition with secondary desiccation at +10° C., (+) data points for samples obtained using freeze-drying condition with secondary desiccation at +25° C., (upright) triangle—control adenoviral stock, (inverted triangle)—negative control degraded adenoviral stock.

The results of this experiment are presented in the tables below:

| Read-outs | | Tg (° C.) | Residual humidity (%) | Osmolality (mOsm/kg) | Hexon infectivity (normalized %) - FIG. 16 | PicoGreen ® test (normalized %) - FIG. 15 | | |
|---|---|---|---|---|---|---|---|---|
| | lyo cycle | | | | T0 | T0 | T1W4 | T1W25 |
| 1 | (2) | 34.5 | 2.9 | 676 | 93 | 4 | 5 | 4 |
| | (1) | 52.7 | 0.9 | 661 | 114 | 6 | 5 | 8 |
| 2 | (2) | 19.6 | 4.0 | 726 | 99 | 2 | 2 | 1 |
| | (1) | 43.4 | 1.3 | 747 | 110 | 3 | 3 | 7 |
| 3 | (2) | 31.3 | 3.3 | 727 | 92 | 3 | 4 | 10 |
| | (1) | 56.3 | 0.9 | 760 | 85 | 5 | 5 | 7 |
| 4 | (2) | 27.2 | 5.0 | 761 | 82 | 1 | 2 | 0 |
| | (1) | 50.3 | 1.1 | 764 | 104 | 3 | | 6 |
| 5 | (2) | 23.7 | 4.1 | 796 | 82 | 3 | 2 | 1 |
| | (1) | 49.9 | 0.9 | 829 | 99 | 3 | 3 | 6 |
| 6 | (2) | 44.0 | 2.7 | 802 | 94 | 5 | 3 | 11 |
| | (1) | 56.5 | 0.8 | 813 | 109 | 4 | 3 | 6 |
| 7 | (2) | 26.3 | 3.7 | 882 | 93 | 2 | 2 | 7 |
| | (1) | 50.6 | 0.9 | 889 | 126 | 2 | 2 | 5 |
| 8 | (2) | 31.7 | 3.9 | 906 | 107 | 3 | 3 | 9 |
| | (1) | 54.1 | 0.9 | 919 | 98 | 3 | 2 | 5 |
| Positive control | | / | / | / | 100 | 0 | | |
| Negative control | | / | / | / | 0 | 100 | | |

-continued

Figure 17:
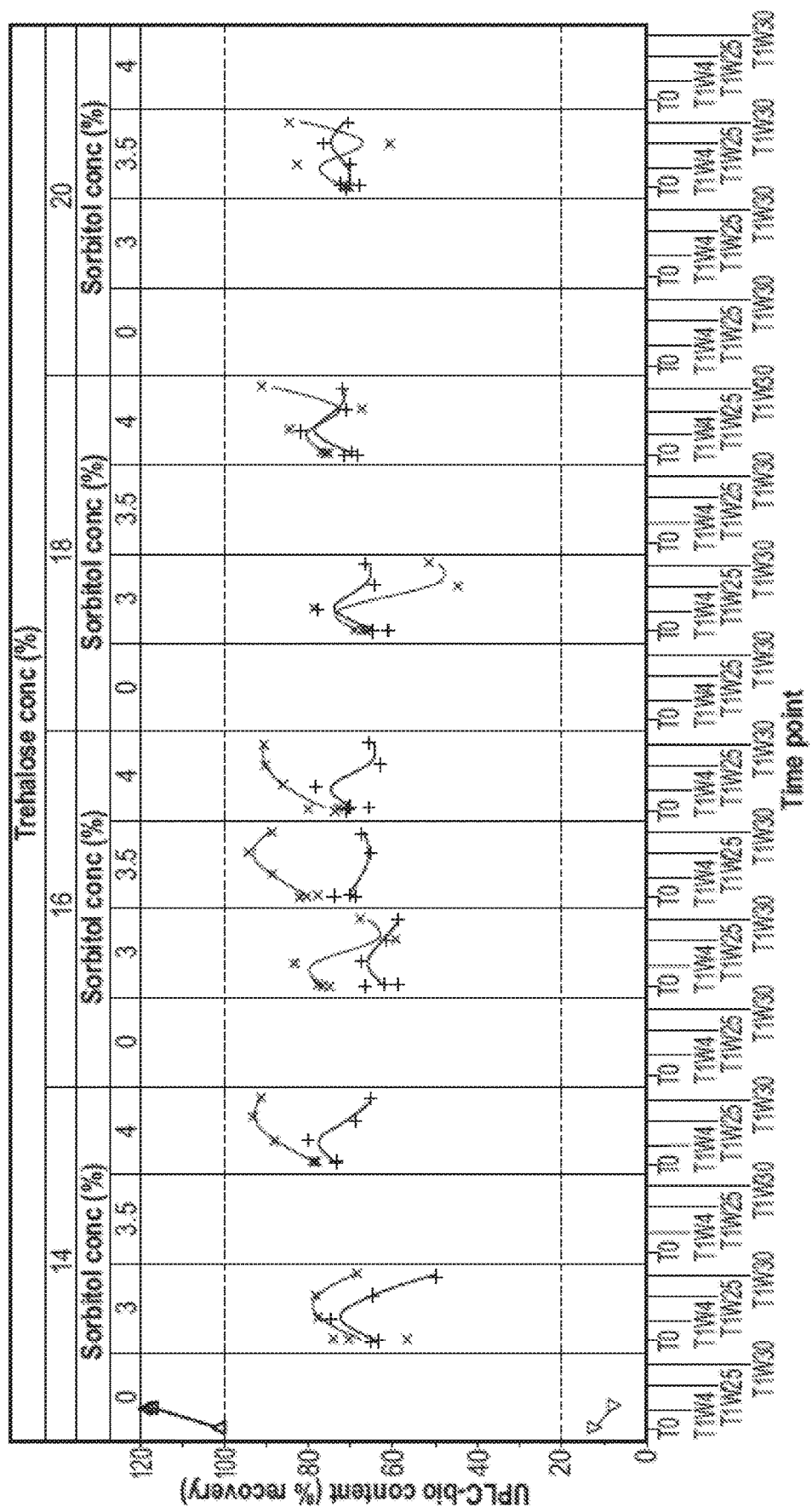
FIG. 17—UPLC data as determined in Example 3: (x) data points for samples obtained using freeze-drying condition with secondary desiccation at +10° C., (+) data points for samples obtained using freeze-drying condition with secondary desiccation at +25° C., (upright triangle)—control adenoviral stock, (inverted triangle)—negative control degraded adenoviral stock.
Figure 18:
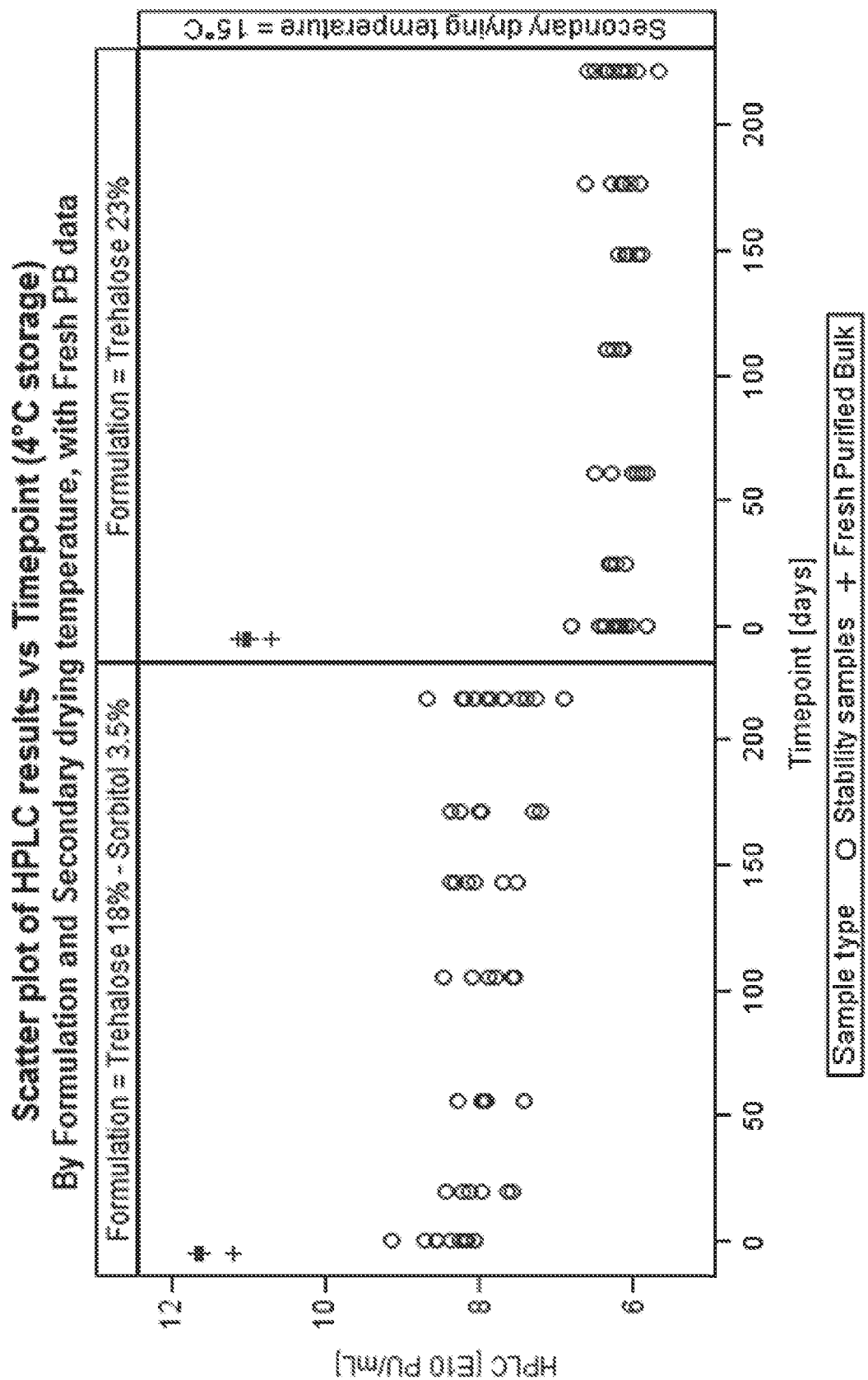
FIG. 18—stability of simian adenovirus as determined by loss estimates due to freeze-drying; comparison of trehalose 18%+sorbitol 3.5% with trehalose 23% at secondary drying temperatures of 15° C. and 25° C.

| Read-outs | | AEX-HPLC content (recovery %) - FIG. 17 | | | CCID50 Infectivity | Ratio HPLC/ infectivity |
| --- | --- | --- | --- | --- | --- | --- |
| | Cycle lyo | T0 | T1W4 | T1W25 | (log) | CCID50 - FIG. 18 |
| 1 | (2) | 68 | 78 | 79 | / | / |
| | (1) | 64 | 75 | 65 | / | / |
| 2 | (2) | 79 | 89 | 94 | 9.0 | 87.4 |
| | (1) | 74 | 80 | 69 | / | / |
| 3 | (2) | 77 | 84 | 60 | / | / |
| | (1) | 63 | 68 | 62 | / | / |
| 4 | (2) | 81 | 89 | 95 | 9.2 | 54.3 |
| | (1) | 71 | 79 | 65 | / | / |
| 5 | (2) | 76 | 87 | 91 | 9.1 | 70.5 |
| | (1) | 69 | 78 | 63 | / | / |
| 6 | (2) | 68 | 79 | 45 | / | / |
| | (1) | 64 | 78 | 64 | / | / |
| 7 | (2) | 76 | 85 | 68 | 8.7 | 166 |
| | (1) | 70 | 82 | 71 | / | / |
| 8 | (2) | 72 | 83 | 61 | 8.4 | 317 |
| | (1) | 71 | 70 | 77 | / | / |
| Positive control | | 102 | 118 | | 9.2 | 70.5 |
| Negative control | | 12 | 8 | | <3.0 | 13730000 |

PicoGreen assay, infectivity HEXON and AEX-HPLC were as described for Example 1. CCID50 infectivity is a measure of adenovirus titer. The Cell Culture Infectious Dose 50 (CCID50) is an end-point dilution assay which quantifies the amount of virus required to produce a cytopathic effect in 50% of cells in a certain volume. In the present example, the titer is expressed in a log 10 scale (Log CCID50/ml). It is measured by inoculating the dilution series samples on indicator cells. After the incubation time (7 days at 37° C. for adenovirus) the adenovirus hexon was immunostained and the results determined microscopically.

The best results taking the overall parameters into account (e.g. PicoGreen value at the lowest, infectivity and HPLC content at the highest, osmolality lower than 900 mOsm/kg) were achieved using freeze-drying cycle 2. Composition 2 (Trehalose 14%-Sorbitol 4%), 4 (Trehalose 16%-Sorbitol 3.5%) and 5 (Trehalose 16%-Sorbitol 4%) performed best on the overall parameters.

Example 4—Stability of Lyophilised Adenovirus

Stability studies on lyophilised compositions were performed over the course of five months at 25° C. or seven months at 15° C. Extrapolation of real time data to three years was also performed using statistical models based on the assumption that degradation would follow a similar profile. Two stability models were used to extrapolate viral content, measured by HPLC and infectivity, measured by fluorescent activated cell sorting (FACS), expressed in international units (IU). (1) Linear model: $\hat{Y}=\alpha_0+\alpha_1 \times Time$; (2) first-order decay model: $\hat{Y}=\beta_1 \times e^{\beta_2 \times Time}$ and (2) first order decay (with asymptote): $\hat{Y}=\beta_0+\beta_1 \times e^{\beta_2 \times Time}$. The measured and extrapolated data are both shown in the following table.

| Secondary Drying Temperature | Formulation | Measured Loss in Freeze-drying (HPLC) | Extrapolation (3 years) | |
| --- | --- | --- | --- | --- |
| | | | Linear Model | First-order Decay Model |
| 15° C. (7 months) | Trehalose 18% + Sorbitol 3.5% | −27% | (−28%) | (−6%) |
| | Trehalose 23% | −43% | +4% | (−3%) |
| 25° C. (5 months) | Trehalose 18% + Sorbitol 3.5% | −32% | (−19%) | (−13%) |
| | Trehalose 23% | −48% | (−21%) | (−4%) |

Figure 19:
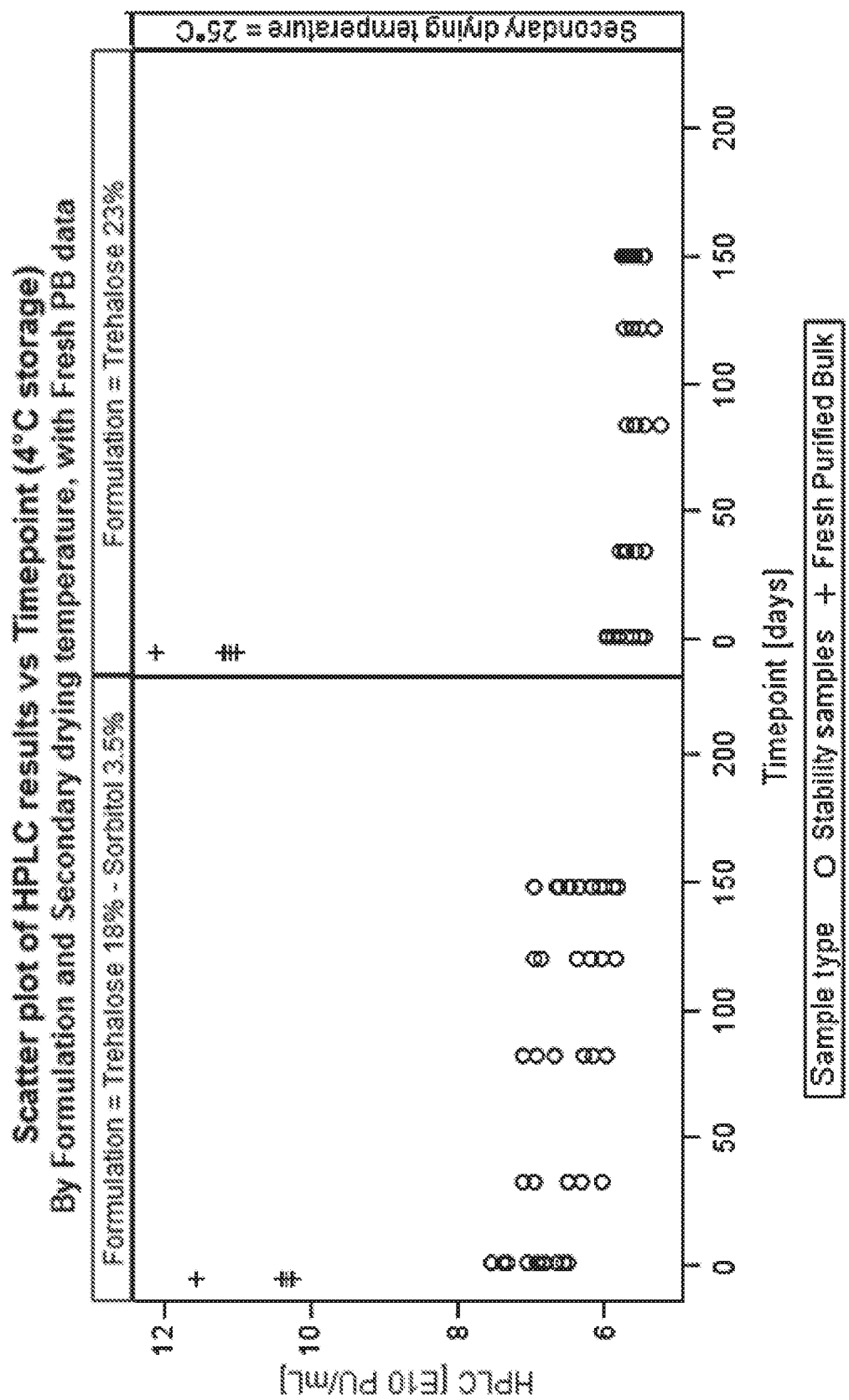
FIG. 19—scatter plot demonstrating the stability of trehalose 18%+sorbitol 3.5% and trehalose 23% at drying temperatures of 15° C. and 25° C. for 200 days.

Secondary drying at 15° C. resulted in greater stability, as measured in loss of adenovirus, than secondary drying at 25° C. Two profiles were observed, as shown in FIGS. 18 and 19. FIG. 18 shows the stability of adenovirus formulated with either 18% trehalose+3.5% sorbitol or 23% trehalose at 4° C. over 200 days, at a secondary drying temperature of 15° C. FIG. 19 shows the stability of adenovirus formulated with either 18% trehalose+3.5% sorbitol or 23% trehalose at 4° C. over the course of 200 days, at a secondary drying temperature of 25° C.

As shown in FIGS. 18 and 19, a concentration of 23% trehalose resulted in a relatively higher loss (approximately 45%) than a concentration of 18% trehalose+3.5% sorbitol upon freeze-drying, with little subsequent loss at 4° C. over time. In contrast, 18% trehalose+3.5% sorbitol resulted in an adenoviral vector loss of only approximately 30%.

Example 5—Physical Stability of Lyophilised Adenovirus

The effect of mechanical stress, replicating vibration stress arising from transport by road and/or air, on the stability of the lyophilised compositions was examined. More particularly, the physical stability of the compositions in the lyophilised state was tested following exposure to shaking stress.

Two formulations were prepared as previously described and tested:
(1) Sucrose 18%+Sorbitol 3.5%
(2) Trehalose 23%

For each test condition, ten glass vials, either siliconized or non-siliconized, containing lyophilised compositions were taped horizontally inside of a lightweight, insulated container (Sofribox) at 4° C. Three replicates were used for each test. The samples were shaken vigorously for two hours at 'Level 2' followed by a further two hours at 'Level 1' using a Lansmont Model 1000 Vibration Test System. The experimental design is intended to replicate the vibration stress encountered during two hours of road transport and two hours of air transport respectively.

Vibration is expected to gradually break down the cake into a powder depending on the cake composition, and the intensity and duration of vibration. The physical integrity of the lyophilised compositions was determined by visual analysis using Axiovision (CQR & photo) at times 0, 2 hours and 4 hours (FIGS. 20 and 21).

FIG. 20 shows the proportion of lyophilised samples that either remained intact (O), were cracked (+) or were fragmented (X) after a simulated transport of two hours via road transport and two hours via air transport. Formulation with 18% trehalose+3.5% sorbitol resulted in lyophilised compositions that were less affected by vibrational stress than formulations with 23% trehalose. A secondary desiccation temperature of 15° C. also resulted in lyophilised compositions that were less affected by vibration stress during transport. Formulation with 18% trehalose+3.5% sorbitol, with a secondary drying temperature of 15° C. and the use of siliconized vials resulted in the best conditions for preserving the lyophilised cakes intact.

FIG. 21 shows the consistency of lyophilised samples that remained not powdery (O), slightly powdery (+) or powdery (X) after a simulated transport of two hours via road transport and two hours via air transport. Formulation with 18% trehalose+3.5% sorbitol resulted in lyophilised compositions that were less affected by vibrational stress than formulations with 23% trehalose. A secondary desiccation temperature of 15° C. also resulted in lyophilised compositions that were less affected by vibration stress during transport. When formulated with 18% trehalose+3.5% sorbitol a secondary drying temperature of 15° C. resulted in less powder formation than a secondary drying temperature of 25° C.

The invention claimed is:

1. A composition comprising a recombinant simian adenoviral vector, sorbitol, an amorphous sugar and NaCl, wherein the amorphous sugar is trehalose, the ratio of sorbitol to trehalose is 4/14 to 3/18 and the concentration of the NaCl is 2.5 mM to 7.5 mM the sorbitol is present in an amount of 3-4% (w/v) and the trehalose is present in an amount of 14-18% (w/v).

2. The composition according to claim 1 wherein the ratio of sorbitol to trehalose is between 4/14 and 3.5/16.

3. The composition according to claim 1, wherein the composition is freeze dried from an aqueous mixture comprising a recombinant simian adenoviral vector, sorbitol, an amorphous sugar and NaCl, wherein the amorphous sugar is trehalose, the ratio of sorbitol to trehalose is 4/14 to 3/18.

4. The composition according to claim 3, wherein the ratio of sorbitol to the amorphous sugar is between 4/14 and 3.5/16.

5. The composition according to claim 3, wherein the concentration of NaCl is 2.5 mM to 5.0 mM.

6. The composition according to claim 3, wherein the amorphous sugar concentration in the aqueous mixture is less than 18% (w/v).

7. The composition according to claim 3, wherein the amorphous sugar concentration in the aqueous mixture is between 10 and 20% (w/v).

8. The composition according to claim 3, wherein the sorbitol concentration in the aqueous mixture is between 3 and 4% (w/v).

9. The composition according to claim 1, wherein the composition further comprises a surfactant.

10. The composition according to claim 9, wherein the surfactant is poloxamer 188 or polysorbate 80.

11. The composition according to claim 1, wherein the composition comprises a buffer selected from one or more of Tris, succinate, borate, Tris-maleate, lysine, histidine, glycine, glycylglycine, citrate, carbonate and phosphate.

12. The composition according to claim 11, wherein the buffer is Tris.

13. The composition according to claim 1, wherein the composition further comprises a bivalent metal ion salt selected from one or more of $MgCl_2$, $CaCl_2$ and $MgSQ_4$.

14. The composition according to claim 13, wherein the bivalent metal ion salt is $MgCl_2$.

15. The freeze dried composition according to claim 3, wherein the composition has a moisture content of 1.40% to 10% (w/w).

16. The composition according to claim 1, wherein the adenoviral vector is a chimpanzee or a bonobo adenoviral vector.

17. The composition according to claim 16, wherein the adenoviral vector is ChAd3, ChAd63, ChAd83, ChAd155, ChAd157, Pan 5, Pan 6, Pan 7 or Pan 9.

18. A kit comprising two containers, wherein the first container contains the freeze-dried composition of claim 3 and the second container contains water for injection.

* * * * *

UNITED STATES PATENT AND TRADEMARK OFFICE
CERTIFICATE OF CORRECTION

| | | |
|---|---|---|
| PATENT NO. | : 11,590,243 B2 | Page 1 of 1 |
| APPLICATION NO. | : 16/478232 | |
| DATED | : February 28, 2023 | |
| INVENTOR(S) | : Erwan Bourles et al. | |

It is certified that error appears in the above-identified patent and that said Letters Patent is hereby corrected as shown below:

In the Claims

Column 28, Line 37, Claim 13:
Change: "selected from one or more of $MgCl_2$, $CaCl_2$ and $MgSQ_4$."
To: -- selected from one or more of $MgCl_2$, $CaCl_2$ and $MgSO_4$. --

Signed and Sealed this
Twenty-fifth Day of April, 2023

Katherine Kelly Vidal
*Director of the United States Patent and Trademark Office*